United States Patent
Howe et al.

(10) Patent No.: US 12,216,128 B2
(45) Date of Patent: Feb. 4, 2025

(54) METHODS FOR GUIDING THERAPY DECISIONS IN SEIZURE DISORDERS

(71) Applicant: Mayo Foundation for Medical Education and Research, Rochester, MN (US)

(72) Inventors: Charles L. Howe, Rochester, MN (US); Benjamin D. Clarkson, Rochester, MN (US); Shailaja Kunda, Rochester, MN (US); Reghann G. LaFrance-Corey, Zumbrota, MN (US); Eric T. Payne, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1064 days.

(21) Appl. No.: 16/976,592

(22) PCT Filed: Apr. 12, 2019

(86) PCT No.: PCT/US2019/027157
§ 371 (c)(1),
(2) Date: Aug. 28, 2020

(87) PCT Pub. No.: WO2019/200213
PCT Pub. Date: Oct. 17, 2019

(65) Prior Publication Data
US 2021/0140974 A1 May 13, 2021

Related U.S. Application Data

(60) Provisional application No. 62/656,664, filed on Apr. 12, 2018.

(51) Int. Cl.
| | |
|---|---|
| *A61K 39/395* | (2006.01) |
| *A61K 38/20* | (2006.01) |
| *A61P 25/08* | (2006.01) |
| *C07K 14/545* | (2006.01) |
| *C07K 14/715* | (2006.01) |
| *C12Q 1/6883* | (2018.01) |
| *G01N 33/68* | (2006.01) |

(52) U.S. Cl.
CPC ..... *G01N 33/6869* (2013.01); *A61K 38/2006* (2013.01); *A61P 25/08* (2018.01); *C12Q 1/6883* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| 6,706,478 B2 | 3/2004 | Duff et al. |
| 2014/0073556 A1 | 3/2014 | Berezin et al. |
| 2017/0007669 A1 | 1/2017 | Sarkar et al. |
| 2017/0204089 A1 | 7/2017 | Kortagere et al. |

FOREIGN PATENT DOCUMENTS

| WO | WO 2016115473 | 7/2016 |
| WO | WO 2017120166 | 7/2017 |
| WO | WO 2018075438 | 4/2018 |

OTHER PUBLICATIONS

EP Extended Search Report in European Appln. No. 19784835.1, dated Apr. 7, 2022, 6 pages.
Gaetano et al., "Preventing epileptogenesis: A realistic goal?," Pharmacol. Research, May 10, 2016, 110:96-100.
Vezzani et al., "Introduction to the 2nd Meeting on Immunity and Inflammation in Epilepsy (IIE2016)," Epilepsia, Jul. 4, 2017, 58(Suppl. 3):7-10.
Aksentijevich et al., "An Autoinflammatory Disease with Deficiency of the Interleukin-1-Receptor Antagonist," N. Engl. J. Medicine, 360(23):2426-2437, Jun. 4, 2009.
Anderson et al., "Alzheimer's and Seizures: Interleukin-18, Indoleamine 2,3-Dioxygenase and. Quinolinic Acid," Int. J. Tryptophan Research, 3:169-173, Oct. 15, 2010.
Anderson et al., "Multiple sclerosis, seizures, and antiepileptics: role of IL-18, IDO, and melatonin," Eur. J. Neurology, 18(5):680-685, May 2011.
Appenzeller et al., "Febrile infection-related epilepsy syndrome (FIRES) is not caused by SCNIA, POLG, PCDH19 mutations or rare copy number variations," Dev. Med. Child Neurology, 54(12):1144-1148, Dec. 2012.
Auvin et al., "Inflammation induced by LPS enhances epileptogenesis in immature rat and may be partially reversed by ILIRA," Epilepsia, 51(S3):34-38, Jul. 2010.
Berg et al, "Revised terminology and concepts for organization of seizures and epilepsies: report of the ILAE Commission on Classification and Terminology, 2005-2009," Epilepsia, 51(4):676-685, Apr. 2010.
Caraballo et al., "Febrile infection-related epilepsy syndrome: a study of 12 patients," Seizure, 22(7):553-559, Sep. 2013.
Clarkson et al., "Functional Deficiency in Endogenous Interleukin-1 Receptor Antagonist in Patients with Febrile Infection-Related Epilepsy Syndrome," Ann. Neurology, 85(4):526-537, Feb. 15, 2019.
Dube et al., "Interleukin-1beta contributes to the generation of experimental febrile seizures," Ann. Neurology, 57(1):152-155, Jan. 2005.

(Continued)

*Primary Examiner* — Christine J Saoud
*Assistant Examiner* — Jon M Lockard
(74) *Attorney, Agent, or Firm* — Fish & Richardson P.C.

(57) ABSTRACT

Materials and methods for identifying subjects as being likely or not likely to respond to an interleukin-1β receptor antagonist (IL-1RA) therapy for a seizure disorder, as well as materials and methods for treating subjects identified as being likely to respond to an IL-1RA therapy for a seizure disorder, are provided herein.

17 Claims, 19 Drawing Sheets
Specification includes a Sequence Listing.

(56) References Cited

OTHER PUBLICATIONS

Eder, "Mechanisms of interleukin-1beta release," Immunobiology, 214(7):543-553, Feb. 2009.
Evans et al., "Action of intracellular IL-1Ra (Type 1) is independent of the IL-1 intracellular signalling pathway," Cytokine, 33(5):274-280, Mar. 7, 2006.
Forget et al., "What is the normal value of the neutrophil-to-lymphocyte ratio?," BMC Res. Notes, 10(1):12, Jan. 3, 2017.
GenBank Accession No. NG_021240.1, "*Homo sapiens* interleukin 1 receptor antagonist (ILIRN), RefSeqGene (LRG_188) on chromosome 2," Apr. 10, 2017, 7 pages.
Giuliani et al., "The P2X7 Receptor-Interleukin-1 Liaison," Front. Pharmacology, 8:123, Mar. 2017, 10 pages.
Greenfeder et al., "Insertion of a structural domain of interleukin (IL)-1 beta confers agonist activity to the IL-1 receptor antagonist. Implications for IL-1 bioactivity," J. Biol. Chemistry, 270(38):22460-22466, Sep. 22, 1995.
Gutierrez et al., "Blood-borne interleukin-1 receptor antagonist crosses the blood-brain barrier," J. Neuroimmunology, 55(2):153-160, Dec. 1994.
Hou et al., "Design of a superior cytokine antagonist for topical ophthalmic use," Proc. Natl. Acad. Sci. USA, 110(10):3913-3918, Mar. 5, 2013.
Howell et al., "Long-term follow-up of febrile infection-related epilepsy syndrome," Epilepsia, 53(1):101-110, Jan. 2012.
Hulkkonen et al., "The balance of inhibitory and excitatory cytokines is differently regulated in vivo and in vitro among therapy resistant epilepsy patients," Epilepsy Research, 59(2-3):199-205, Apr./May 2004.
Iori et al., Blockade of the IL-1R1/TLR4 pathway mediates disease-modification therapeutic effects in a model of acquired epilepsy, Neurobiol. Disease, 99:12-23, Mar. 2017.
Jeong et al., "IL-1ra Secreted by ATP-Induced P2Y2 Negatively Regulates MUC5AC Overproduction via PLCbeta3 during Airway Inflammation," Hindawi Mediators of Inflammation, 2016:7984853, Feb. 2016, 11 pages.
Jesus et al., "A novel mutation of IL1RN in the deficiency of interleukin-1 receptor antagonist syndrome: description of two unrelated cases from Brazil," Arthritis & Rheumatism, 63(12):4007-4017, Dec. 2011.
Kanemoto et al., "Interleukin (IL)-1β, IL-1α, and IL-1 receptor antagonist gene polymorphisms in patients with temporal lobe epilepsy," Ann. Neurology, 47(5):571-574, May 2000.
Kenney-Jung et al., "Febrile infection-related epilepsy syndrome treated with anakinra," Ann. Neurology, 80(6):939-945, Dec. 2016.
Kramer et al., "Febrile infection-related epilepsy syndrome (FIRES): does duration of anesthesia affect outcome?," Epilepsia, 52(s8):28-30, Oct. 2011.
Kramer et al., "Febrile infection-related epilepsy syndrome (FIRES): pathogenesis, treatment, and outcome: a multicenter study on 77 children," Epilepsia, 52(11):1956-1965, Nov. 2011.
Lehtimaki et al., "Levels of IL-1beta and IL-1ra in Cerebrospinal Fluid of Human Patients after Single and Prolonged Seizures," NeuroImmunoModulation, 17(1):19-22, 2010.
Lopez-Castejon et al., "Understanding the mechanism of IL-1beta secretion," Cytokine & Growth Factor Reviews, 22(4):189-195, Aug. 2011.
Marchi et al., "Antagonism of peripheral inflammation reduces the severity of status epilepticus," Neurobiol. Disease, 33(2):171-181, Feb. 2009.
Mazzuca et al., "18F-FDG PET Reveals Frontotemporal Dysfunction in Children with Fever-Induced Refractory Epileptic Encephalopathy," J. Nucl. Medicine, 52(1):40-47, Jan. 2011.
McIntyre et al., "Inhibition of Interleukin 1 (IL-1) Binding and Bioactivity In Vitro and Modulation of Acute Inflammation In Vivo by IL-1 Receptor Antagonist and Anti-IL-1 Receptor Monoclonal Antibody," J. Exp. Medicine, 173(4):931-939, Apr. 1, 1991.

Noe et al., "Pharmacological blockade of IL-1beta/IL-1 receptor type 1 axis during epileptogenesis provides neuroprotection in two rat models of temporal lobe epilepsy," Neurobiol. Disease, 59:183-193, Nov. 2013.
Patil et al., "Clinical profile and treatment outcome of febrile infection-related epilepsy syndrome in South Indian children," Ann. Indian Acad. Neurology, 19(2):188-194, Apr.-Jun. 2016.
PCT International Preliminary Report on Patentability in International Appln. No. PCT/US2019/027157, dated Oct. 13, 2020, 8 pages.
PCT International Search Report and Written Opinion in International Appln. No. PCT/US2019/027157, dated Jul. 10, 2019, 12 pages.
Piccioli et al., "The secretion of IL-1beta and options for release," Semin. Immunology, 25(6):425-429, Dec. 15, 2013.
Qu et al., "Nonclassical IL-1beta Secretion Stimulated by P2X7 Receptors Is Dependent on Inflammasome Activation and Correlated with Exosome Release in Murine Macrophages," J. Immunology, 179(3): 1913-1925, Aug. 1, 2007.
Reddy et al., "An Autoinflammatory Disease Due to Homozygous Deletion of the IL1RN Locus," N. Engl. J. Medicine, 360(23):2438-2444, Jun. 4, 2009.
Semple et al., "Interleukin-1 Receptor in Seizure Susceptibility after Traumatic Injury to the Pediatric Brain," J. Neuroscience, 37(33):7864-7877, Aug. 16, 2017.
Shakoory et al., "Interleukin-1 Receptor Blockade Is Associated With Reduced Mortality in Sepsis Patients With Features of Macrophage Activation Syndrome: Reanalysis of a Prior Phase III Trial," Crit. Care Medicine, 44(2):275-281, Feb. 2016.
Turola et al., "Microglial microvesicle secretion and intercellular signaling," Front. Physiology, 3:149, May 22, 2012, 11 pages.
van Baalen et al., "Febrile infection-related epilepsy syndrome (FIRES): A nonencephalitic encephalopathy in childhood," Epilepsia, 51(7):1323-1328, Jul. 2010.
Vezzani et al, "Inflammation and Epilepsy," Epilepsy Currents, 5(1):1-6, Jan. 1, 2005.
Vezzani et al., "Functional Role of Inflammatory Cytokines and Antiinflammatory Molecules in Seizures and Epileptogenesis," Epilepsia, 43(s5):30-35, Jul. 24, 2002.
Vezzani et al., "IL-1 receptor/Toll-like receptor signaling in infection, inflammation, stress and neurodegeneration couples hyperexcitability and seizures," Brain Behav. Immunity, 25(7):1281-1289, Oct. 2011.
Vezzani et al., "New Roles for Interleukin-1 Beta in the Mechanisms of Epilepsy," Epilepsy Currents, 7(2):45-50, Mar. 2007.
Vezzani et al., "Powerful anticonvulsant action of IL-1 receptor antagonist on intracerebral injection and astrocytic overexpression in mice," Proc. Natl. Acad. Sci. USA, 97(21):11534-11539, Oct. 10, 2000.
Walker et al., "WONOEP appraisal: Molecular and cellular biomarkers for epilepsy," Epilepsia, 57(9):1354-1362, Jul. 4, 2016.
Wilson et al., "Secretion of Intracellular IL-1 Receptor Antagonist (Type 1) Is Dependent on P2X7 Receptor Activation," J. Immunology, 173(2):1202-1208, Jul. 15, 2004.
Witkin et al., "Influence of Interleukin-1 Receptor Antagonist Gene Polymorphism on Disease," Clin. Infect. Diseases, 34(2):204-209, Jan. 15, 2002.
Yu et al., "Modulation of Immunity and the Inflammatory Response: A New Target for Treating Drug-resistant Epilepsy," Curr. Neuropharmacology, 11(1):114-127, Jan. 2013.
Altiok et al., "A novel mutation in the interleukin-1 receptor antagonist associated with intrauterine disease onset," Clin. Immunol., Oct. 2012, 145(1):77-81.
Deb et al., "Functional characterization of mouse spinal cord infiltrating CD8+ lymphocytes," J. Neuroimmunol., Sep. 2009, 214(1-2):33-42.
DeSena et al., "Systemic autoinflammation with intractable epilepsy managed with interleukin-1 blockade," J. Neuroinflammation, Feb. 2018, 15(1):38.
Desmet et al., "Human Splicing Finder: an online bioinformatics tool to predict splicing signals," Nucleic Acids Res., May 2009, 37(9):e67.

(56) References Cited

OTHER PUBLICATIONS

Farias-Moeller et al., "A Practical Approach to Ketogenic Diet in the Pediatric Intensive Care Unit for Super-Refractory Status Epilepticus," Neurocrit. Care, Apr. 2017, 26(2):267-272.

Farias-Moeller et al., "Early ictal and interictal patterns in FIRES: The sparks before the blaze," Epilepsia, Aug. 2017, 58(8):1340-1348.

Farias-Moeller et al., "Fueling the FIRES: Hemophagocytic lymphohistiocytosis in febrile infection-related epilepsy syndrome," Epilepsia, Sep. 2018, 59(9):1753-1763.

Gaspard et al., "New-onset refractory status epilepticus (NORSE) and febrile infection-related epilepsy syndrome (FIRES): State of the art and perspectives," Epilepsia, Apr. 2018, 59(4):745-752.

Hirsch et al., "Proposed consensus definitions for new-onset refractory status epilepticus (NORSE), febrile infection-related epilepsy syndrome (FIRES), and related conditions," Epilepsia, Apr. 2018, 59(4):739-744.

Hon et al., "Febrile Infection-Related Epilepsy Syndrome (FIRES): An Overview of Treatment and Recent Patents," Recent Pat. Inflamm. Allergy Drug Discov., 2018, 12(2):128-135.

Jun et al., "Tocilizumab treatment for new onset refractory status epilepticus," Ann. Neurol., Dec. 2018, 84(6):940-945.

Lewandowska, "The missing puzzle piece: splicing mutations," Int. J. Clin. Exp. Pathol., Nov. 2013, 6(12):2675-2682.

Luotola et al., "Associations between interleukin-1 (IL-1) gene variations or IL-1 receptor antagonist levels and the development of type 2 diabetes," J. Intern. Med., Mar. 2011, 269(3):322-332.

Luotola et al., "Genetic variation of the interleukin-1 family and nongenetic factors determining the interleukin-1 receptor antagonist phenotypes," Metabolism, Oct. 2010, 59(10):1520-1527.

Nabbout et al., "Acute encephalopathy with inflammation-mediated status epilepticus," Lancet Neurol., Jan. 2011, 10(1):99-108.

Rafiq et al., "Common genetic variation in the gene encoding interleukin-1-receptor antagonist (IL-1RA) is associated with altered circulating IL-1RA levels," Genes Immun., Jun. 2007, 8(4):344-351.

Rao et al., "Pathogen-Mediated Inhibition of Anorexia Promotes Host Survival and Transmission," Cell, Jan. 2017, 168(3):503-516.e12.

Saitoh et al., "Cytokine-related and sodium channel polymorphism as candidate predisposing factors for childhood encephalopathy FIRES/AERRPS," J. Neurol. Sci., Sep. 2016, 368:272-276.

Sakuma et al., "Intrathecal overproduction of proinflammatory cytokines and chemokines in febrile infection-related refractory status epilepticus," J. Neurol. Neurosurg. Psychiatry, Jul. 2015, 86(7):820-822.

Sculier et al., "New onset refractory status epilepticus (NORSE)," Seizure, May 2019, 68:72-78.

Ulusoy et al., "Interleukin-1 receptor antagonist deficiency with a novel mutation; late onset and successful treatment with canakinumab: a case report," J. Med. Case Rep., Jun. 2015, 9:145.

Carter et al., "The interleukin 1 receptor antagonist gene allele 2 as a predictor of pouchitis following colectomy and IPAA in ulcerative colitis," Gastroenterology, Oct. 2001, 121(4):805-811.

Dinarello, "Why not treat human cancer with interleukin-1 blockade?," Cancer Metastasis Rev., Jun. 2010, 29(2):317-329.

Greco et al., "Microenvironmental considerations in the application of human mesenchymal stem cells in regenerative therapies," Biologics, Dec. 2008, 2(4):699-705.

Isoda et al., "Deficiency of Interleukin-1 Receptor Antagonist Promotes Neointimal Formation After Injury," Circulation, Jul. 2003, 108(5):516-518.

Lavalette et al., "Interleukin-1β Inhibition Prevents Choroidal Neovascularization and Does Not Exacerbate Photoreceptor Degeneration," Am. J. Pathol., May 2011, 178(5):2416-2423.

Niklander et al., "IL-1/IL-1R Signaling in Head and Neck Cancer," Front. Oral Health, Aug. 2021, 2:722676.

Ortiz et al., "Interleukin 1 receptor antagonist mediates the antiinflammatory and antifibrotic effect of mesenchymal stem cells during lung injury," Proc. Natl. Acad. Sci. USA, Jun. 2007, 104(26):11002-11007.

Shikama et al., "Palmitate-stimulated monocytes induce adhesion molecule expression in endothelial cells via IL-1 signaling pathway," J. Cell. Physiol., Mar. 2015, 230(3):732-742.

Staros, "Molecular discoveries alter our view of inflammatory bowel disease. A review from scientific, clinical, and laboratory perspectives," Am. J. Clin. Pathol., Apr. 2003, 119(4):524-539.

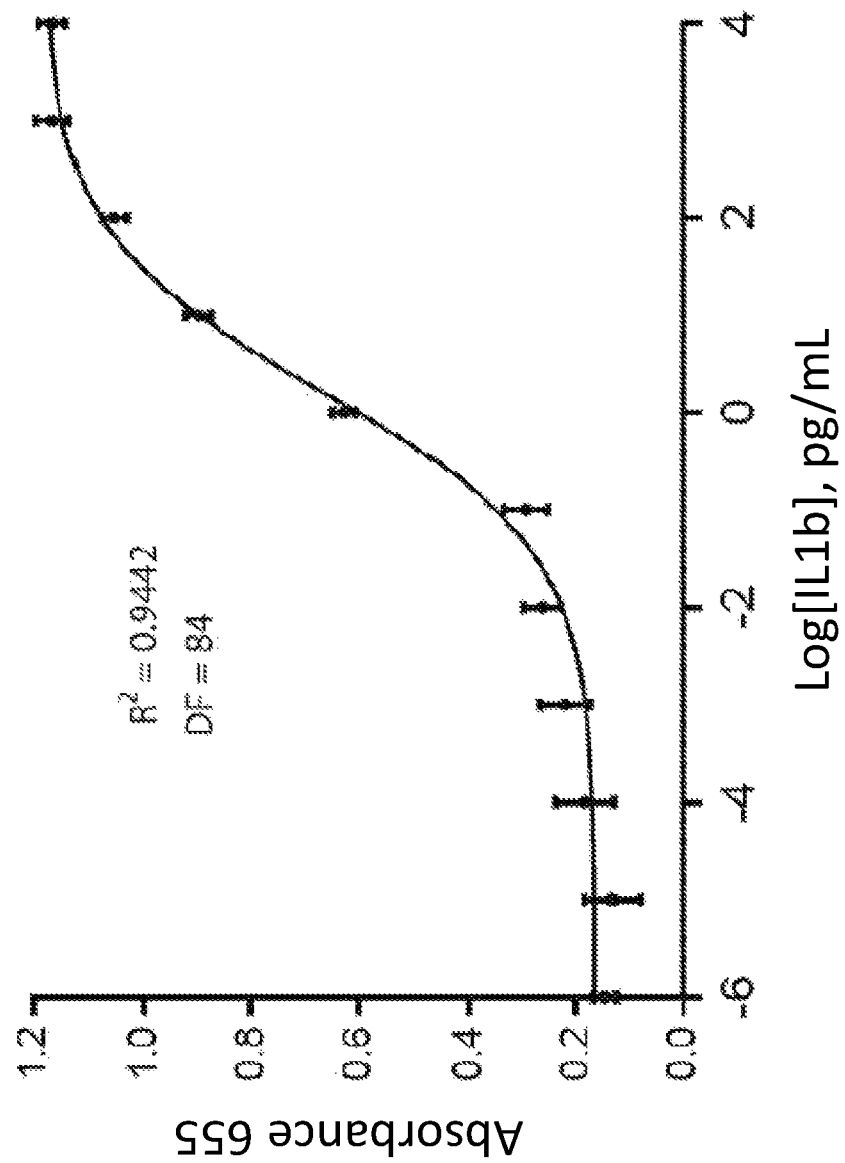

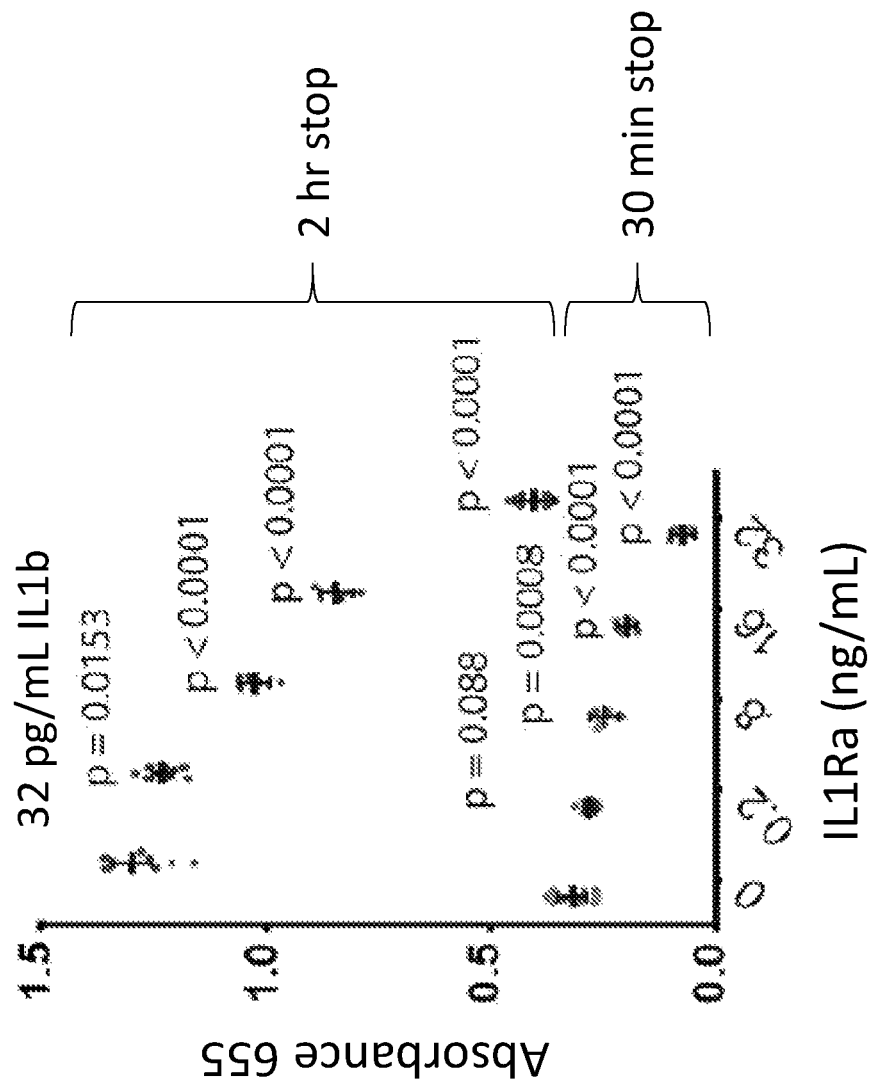

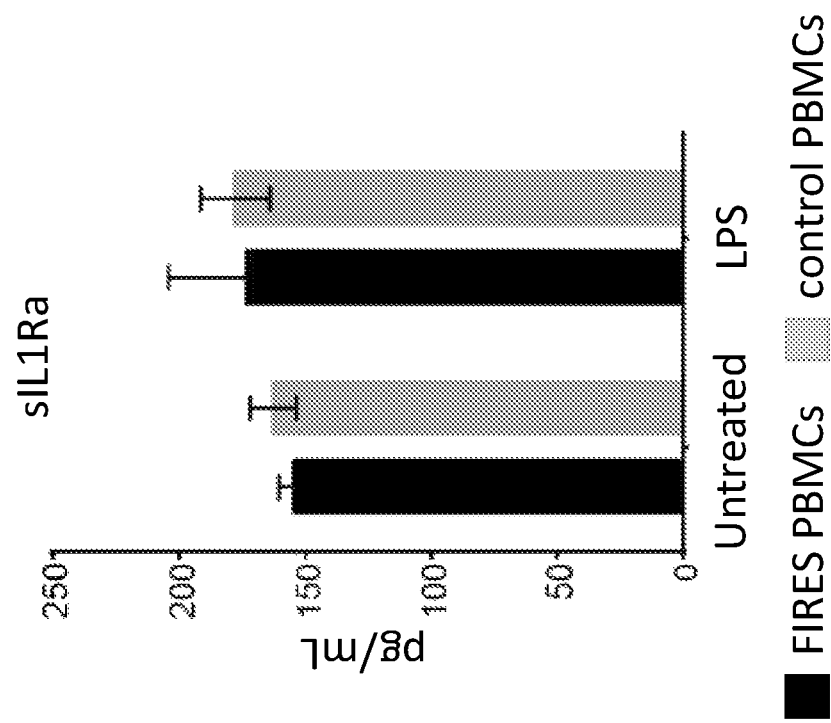

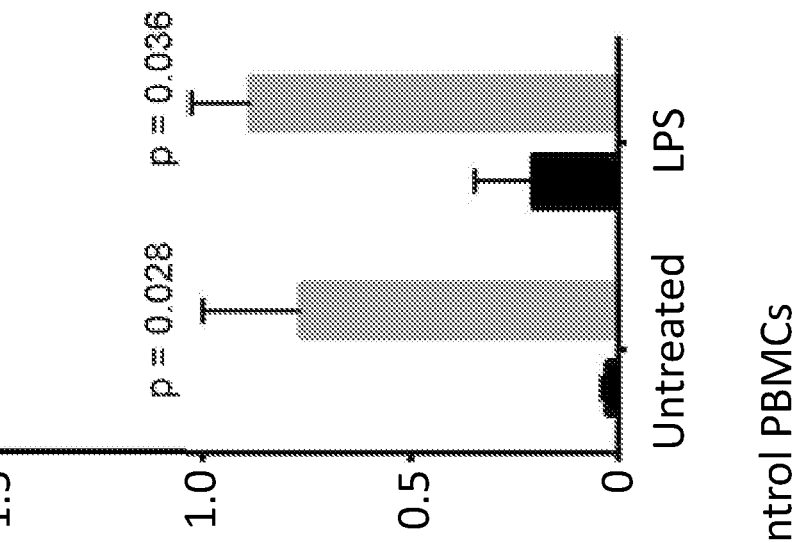
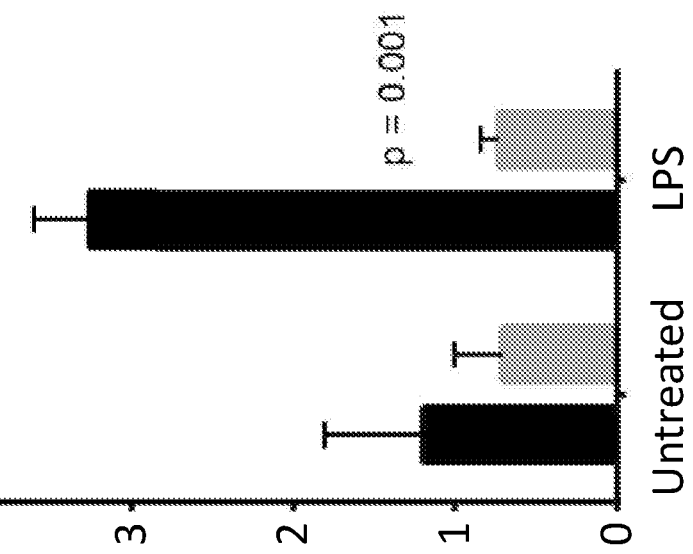
FIG. 7A
FIG. 7B

METHODS FOR GUIDING THERAPY DECISIONS IN SEIZURE DISORDERS

CROSS-REFERENCE TO RELATED APPLICATIONS

This application is a National Stage application under 35 U.S.C. § 371 of International Application No. PCT/US2019/027157 having an International Filing Date of Apr. 12, 2019, which claims benefit of priority from U.S. Provisional Application No. 62/656,664, filed on Apr. 12, 2018. The disclosures of the prior applications are considered part of (and are incorporated by reference in) the disclosure of this application.

TECHNICAL FIELD

This document relates to materials and methods for identifying subjects as being likely or not likely to respond to an interleukin-1β receptor antagonist (IL-1RA) therapy for a seizure disorder, as well as materials and methods for treating subjects identified as being likely to respond to an IL-1RA therapy for a seizure disorder.

BACKGROUND

The sudden, catastrophic onset of severe refractory status epilepticus in a child who has recently experienced an apparently resolved febrile illness is referred to as "FIRES," which historically has stood for "fever-initiated refractory encephalopathies," "febrile infection responsive epileptic encephalopathies of school age," "febrile infection-related epilepsy syndrome," and "fulminant immune response epilepsy syndrome." As used herein, the term "FIRES" stands for "fulminant inflammatory refractory epilepsy syndrome," based on the lack of an adaptive or autoimmune component and the general failure of patients to respond to therapies that target lymphocytes and antibodies. FIRES can be classified as a true post-infectious seizure syndrome. Although the occurrence of FIRES is relatively rare, it serves as an extreme example of a broad spectrum of epilepsies arising from aberrant inflammatory responses.

There is no clear diagnostic profile that can be used to guide decision making for selecting the appropriate therapeutic target for FIRES and other seizure disorders. FIRES exhibits an extraordinarily high level of seizure activity, making it challenging to reduce seizure burden. As a diagnosis of exclusion, effective treatment often lags behind the peak of seizure activity. Burst-suppression coma, midazolam, high dose phenobarbital, ketogenic diet, and cannabidiol therapy may be effective to treat at least some FIRES patients, but none of these interventions has proven universally effective. Despite typically massive polytherapy, outcomes generally are poor, with substantial mortality and high likelihood of moderate to severe mental retardation and severe lifelong cognitive impairment. In addition, nearly all patients have refractory epilepsy after the initial phase.

SUMMARY

This document is based, at least in part, on the discovery that IL-1RA function is deficient in some patients with seizure disorders, and that such patients can benefit from treatment with therapies such as anakinra, a recombinant form of IL-1RA. For example, subjects with a seizure disorder such as FIRES, periodic autoinflammatory seizure syndrome (PASS), deficiency of IL-1RA (DIRA), or other medically refractory epilepsy (MRE) who demonstrate a deficiency in IL-1RA function, with or without normal IL-1RA production, can benefit from treatment with anakinra or other therapies that increase IL-1RA function or attenuate IL-1R inflammatory signaling.

In a first aspect, this document features a method for identifying a subject having a seizure disorder as being likely to respond to treatment that attenuates IL-1R inflammatory signaling. The method can include determining that the subject has decreased IL-1RA function as compared to a control level of IL-1RA function, and identifying the subject as being likely to respond to treatment that attenuates IL-1R inflammatory signaling. The treatment can include an IL-1RA replacement therapy (e.g., anakinra) or an IL-1RA supplementation therapy. The seizure disorder can be FIRES, FIRES, PASS, DIRA, or MRE. The subject can be a human child. The control level of IL-1RA function can be the level of IL-1RA function in corresponding normal subjects who do not have the seizure disorder. The determining can include measuring IL-1RA activity in a biological sample from the subject, where the biological sample includes serum, serum microvesicles, or CSF, and determining that the IL-1RA activity in the biological sample is decreased relative to a corresponding control level of IL-1RA activity. The determining can include measuring an inflammatory response in primed and stimulated neutrophils, monocytes or peripheral blood mononuclear cells (PBMCs) isolated from the subject, and determining that the measured inflammatory response is higher than an inflammatory response for control primed and stimulated neutrophils, monocytes, or PBMCs from subjects who do not have the seizure disorder. The method can include determining that the measured inflammatory response is at least two standard deviations higher than the inflammatory response for control primed and stimulated neutrophils, monocytes, or PBMCs from subjects who do not have the seizure disorder. The inflammatory response can include secretion of IL-1β, IL-1RA, IL-18, IL-33, IL-36, IL-37, or IL-38 from the neutrophils, monocytes, or PBMCs after stimulation. The method can include priming the neutrophils, monocytes, or PBMCs with lipopolysaccharide (LPS) and/or stimulating the neutrophils, monocytes, or PBMCs with ATP. The determining can include measuring the relative amounts of IL-1RA (protein) or IL1RN (mRNA) isoforms in a biological sample from the subject, and determining that the subject has a ratio of soluble IL-1RA:intracellular IL-1RA that is increased relative to a control ratio of soluble IL-1RA:intracellular IL-1RA. The control ratio of soluble IL-1RA:intracellular IL-1RA can the ratio of soluble IL-1RA:intracellular IL-1RA in control subjects not having the seizure disorder.

In another aspect, this document features a method for treating a subject having a seizure disorder. The method can include identifying the subject as having decreased IL-1RA function as compared to the level of IL-1RA function in corresponding normal subjects who do not have the seizure disorder, and administering to the subject a treatment that attenuates IL-1R inflammatory signaling. The treatment can include an IL-1RA replacement therapy (e.g., anakinra) or an IL-1RA supplementation therapy. The seizure disorder can be FIRES, PASS, DIRA, or MRE. The subject can be a human child. The control level of IL-1RA function can be the level of IL-1RA function in corresponding normal subjects who do not have the seizure disorder. The determining can include measuring IL-1RA activity in a biological sample from the subject, where the biological sample includes serum, serum microvesicles, or CSF, and determining that the IL-1RA activity in the biological sample is decreased relative to a corresponding control level of IL-1RA activity. The determining can include measuring an inflammatory response in primed and stimulated neutrophils, monocytes, or PBMCs isolated from the subject, and determining that the measured inflammatory response is higher than an inflammatory response for control primed and stimulated neutrophils, monocytes, or PBMCs from subjects who do not have the seizure disorder. The method can include determining that the measured inflammatory response is at least two standard deviations higher than the inflammatory response for control primed and stimulated neutrophils, monocytes, or PBMCs from subjects who do not have the seizure disorder. The inflammatory response can include secretion of IL-1β, IL-1RA, IL-18, IL-33, IL-36, IL-37, or IL-38 from the neutrophils, monocytes, or PBMCs after stimulation. The method can include priming the neutrophils, monocytes, or PBMCs with LPS and/or stimulating the neutrophils, monocytes, or PBMCs with ATP. The determining can include measuring the relative amounts of IL-1RA (protein) or IL1RN(mRNA) isoforms in a biological sample from the subject, and determining that the subject has a ratio of soluble IL-1RA:intracellular IL-1RA that is increased relative to a control ratio of soluble IL-1RA:intracellular IL-1RA. The control ratio of soluble IL-1RA:intracellular IL-1RA can be the ratio of soluble IL-1RA:intracellular IL-1RA in control subjects not having the seizure disorder.

In another aspect, this document features a method for identifying a subject having a seizure disorder as being likely to respond to treatment that attenuates IL-1R inflammatory signaling. The method can include determining that the subject exhibits a level of functional IL-1RA antagonism that is decreased below a predetermined threshold level of functional IL-1RA antagonism, and identifying the subject as being likely to respond to treatment that attenuates IL-1R inflammatory signaling. The treatment can include an IL-1RA replacement therapy (e.g., anakinra) or an IL-1RA supplementation therapy. The seizure disorder can be FIRES, PASS, DIRA, or MRE. The subject can be a human child. The threshold level can be 10% of the level of functional IL-1RA antagonism in corresponding control subjects who do not have the seizure disorder.

In yet another aspect, this document features a method for treating a subject having a seizure disorder. The method can include identifying the subject as having a level of functional IL-1RA antagonism that is decreased below a predetermined threshold level of functional IL-1RA antagonism, and administering to the subject a treatment that attenuates IL-1R inflammatory signaling. The treatment can include an IL-1RA replacement therapy (e.g., anakinra) or an IL-1RA supplementation therapy. The seizure disorder can be FIRES, PASS, DIRA, or MRE. The subject can be a human child. The threshold level can be 10% of the level of functional IL-1RA antagonism in corresponding control subjects who do not have the seizure disorder.

This document also features a method for identifying a subject as being at risk for experiencing a seizure disorder. The method can include determining that the subject has decreased IL-1RA function as compared to a control level of IL-1RA function, and identifying the subject as having an increased likelihood of experiencing a seizure disorder. The subject can be a human child. The control level of IL-1RA function can be the level of IL-1RA function in corresponding normal subjects who do not have the seizure disorder. The determining can include measuring IL-1RA activity in a biological sample from the subject, where the biological sample includes serum, serum microvesicles, or CSF, and determining that the IL-1RA activity in the biological sample is decreased relative to a corresponding control level of IL-1RA activity. The determining can include measuring an inflammatory response in primed and stimulated neutrophils, monocytes, or PBMCs isolated the subject, and determining that the measured inflammatory response is higher than an inflammatory response for control primed and stimulated neutrophils, monocytes, or PBMCs from subjects who do not have the seizure disorder. The method can include determining that the measured inflammatory response is at least two standard deviations higher than the inflammatory response for control primed and stimulated neutrophils, monocytes, or PBMCs from subjects who do not have the seizure disorder. The inflammatory response can include secretion of IL-1β, IL-1RA, IL-18, IL-33, IL-36, IL-37, or IL-38 from the neutrophils, monocytes, or PBMCs after stimulation. The method can include priming the neutrophils, monocytes, or PBMCs with LPS, and/or stimulating the neutrophils, monocytes, or PBMCs with ATP. The determining can include measuring the relative amounts of IL-1RA (protein) or IL1RN (mRNA) isoforms in a biological sample from the subject, and determining that the subject has a ratio of soluble IL-1RA:intracellular IL-1RA that is increased relative to a control ratio of soluble IL-1RA:intracellular IL-1RA. The control ratio of soluble IL-1RA:intracellular IL-1RA can be the ratio of soluble IL-1RA:intracellular IL-1RA in control subjects not having the seizure disorder.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A shows serum IL-1RA levels and FIG. 1B shows serum IL-1β levels detected by ELISA in healthy controls and patients with episodic focal epilepsy, FIRES, or ESE, as indicated. FIG. 1C show CSF IL-1RA levels and FIG. 1D shows CSF IL-1β levels detected by ELISA in patients with normal pressure hydrocephalus (NPH) (controls), as well as in patients with episodic focal epilepsy, FIRES, or ESE, as indicated. Error bars indicate standard error of the mean.

FIGS. 2A-2D are a series of graphs plotting various components in the development of an IL-1R signaling cell-based assay. In all experiments, HEK-Blue IL1R supernatants were collected 24 hours after treatment and mixed with prewarmed Quanti-Blue detection reagent. Absorption at 655 nm was read after 3 hours. Background absorbance values have been subtracted from panels 2B-2D. FIG. 2A is a graph plotting a dose response curve for HEK-Blue IL1R cells treated with IL-1β (1 ag/mL to 10 ng/mL) to determine the lower and upper limits of detection. A log agonist vs. response curve (non-linear least squares fit) is shown, based on a four parameter variable slope model (Hill equation). FIGS. 2B and 2C are graphs plotting HEK-Blue IL1R cells were treated with 0-128 pg/mL IL-1β in the presence of 0-200 ng/ml IL-1RA to determine an optimal IL-1β concentration that maximized the signal to noise ratio while also allowing for low dose inhibition by IL-1RA. FIG. 2D is a graph plotting the inhibitory effect of IL-1RA on HEK-Blue IL1R cells that were treated for 30 minutes or 2 hours with 32 pg/mL IL-1β, in combination with the indicated concentrations of IL-1RA. After the treatment period, further IL1R-IL-1β binding was blocked with saturating concentrations of IL-1RA (1 μg/mL), and supernatants were collected 24 hours after the initial treatment. Multiple comparison corrected One-Way ANOVA P values (Dunnett) are indicated, compared to the no IL-1RA condition.

FIG. 3A is a graph plotting HEK IL1R cell IL-1R activity in cells treated with 10% serum from healthy controls (HC), focal epilepsy (FE) patients, FIRES patients, and patients with electrical status epilepticus in sleep (ESES) for 2 hours before quenching with excess IL-1RA as described in FIG. 2. FIG. 3B shows HEK IL1R activity elicited by 32 pg/mL IL-1β in in the presence of 10% of the indicated serum. HEK IL1R activity from the experiment in FIG. 3B is plotted against the final serum IL-1β (FIG. 3C) or IL-1RA (FIG. 3D) levels. In FIG. 3E, HEK IL1R cells were treated as in FIG. 3B with the indicated concentrations of IL-1RA. Means with 95% confidence intervals are plotted (FIGS. 3A, 3B, and 3E). Mean values are traced in FIGS. 3C and 3D. Multiple comparison corrected One-Way ANOVA P values (Dunnett) are indicated compared to HC serum condition (FIGS. 3A-3B). P values in FIGS. 3C and 3D indicate whether the slope is significantly non-zero.

FIG. 4B). In FIGS. 4C-4D, HEK-Blue IL1R cells were treated with 32 pg/mL IL-1β with or without 650 pg/mL IL-1RA in media supplemented with or without 50% aCSF, 50% NPH CSF, or 50% dialyzed NPH CSF (dCSF). Multiple comparison corrected One-Way ANOVA P values (Dunnett) are indicated compared to the no IL-1β condition (FIG. 4A) and the no IL-1RA condition (FIGS. 4C-4D). Error bars represent 95% confidence intervals. Data are representative of 2-3 independent experiments.

FIG. 5A is a graph plotting HEK IL-1R activity after treatment with 32 pg/mL IL-1β in media alone or in the presence of 65 pM IL-1RA, 50% dialyzed FIRES patient pre-treatment CSF containing 65 pM patient IL-1RA, 50% dialyzed NPH CSF supplemented with 650 pM IL-1RA, or 50% dialyzed FIRES patient post-treatment CSF containing 1.3 nM IL-1RA. FIG. 5B is a graph plotting HEK IL-1R activity in cells treated with 32 pg/mL IL-1β in the presence of 50% dialyzed NPH CSF supplemented prior to dialysis with or without 65 pM IL-1RA. In FIG. 5C, HEK—Blue IL1R cells were treated with 10% NPH CSF or FIRES patient CSF. ***P<0.0001, *P<0.05. Multiple comparison corrected P values (Holm-Sidak) are indicated for all significant findings using One-Way ANOVA (FIG. 5A) or two-tailed Student's t-test (FIGS. 5B and 5C). Unless otherwise indicated, P values denote significance for comparisons made to the control (0 IL-1RA) condition. Error bars represent 95% confidence intervals.

FIGS. 6A-6C are a series of graphs plotting levels of soluble IL-1RA (sIL1Ra), intracellular IL-1RA (icIL1Ra), and IL-1RA mRNA expression in FIRES patient PBMCs. Freshly isolated FIRES patient or control PBMCs were treated as indicated for 6-24 hours, and IL-1RA protein (FIGS. 6A and 6B) and mRNA (FIG. 6C) expression were analyzed by RT-PCR. Briefly, PBMC supernatants were collected after treatment, cells were washed, and cell pellets were lysed. Intracellular IL-1RA (icIL1RA) concentration in supernatants and lysates was then determined by ELISA. Relative mRNA expression was calculated by normalization to baseline samples. Values are averaged from technical duplicates (ELISA) or triplicates (RTPCR) representing n=2-6 samples. Student's t-test p values are shown for all significant findings. Error bars indicate standard error of the mean.

FIGS. 7A-7F are a series of graphs plotting the relative expression of IL1RN isoforms in FIRES patient PBMCs. Freshly isolated FIRES patient or control PBMCs were treated as indicated for 6-24 hours, and IL1RN isoform expression was analyzed by RT-PCR using a specific forward primer and common reverse primer for each isoform. Relative mRNA expression was calculated by normalization to baseline samples. FIG. 7A, IL1RN isoform 1; FIG. 7B, IL1RN isoform 2; FIG. 7C, IL1RN isoform 3, and FIG. 7D, IL1RN isoform 4/5. As shown in FIGS. 7E and 7F, expression of each isoform was normalized to aggregate IL1RN expression levels, which was calculated in arbitrary units relative to GAPDH expression. Average values from technical triplicates are presented. Student's t-test p values are shown for all significant findings. Error bars indicate standard error of the mean.

FIG. 8A shows that LPS priming drove release of TNFα, IL-6, and IL-8, but did not directly induce IL-1β release. FIG. 8B is a graph plotting IL-1β release from unprimed or primed neutrophils stimulated with different concentrations of ATP.

Unprimed cells showed no response to ATP at any concentration (triangles and dashed line), but primed cells exhibited robust IL-1β production and release at higher ATP concentrations (circles and solid line). A 3-parameter sigmoidal curve (gray line) fit to the ATP response data was used to determine the $EC_{50}$ for ATP.

Figure 9:
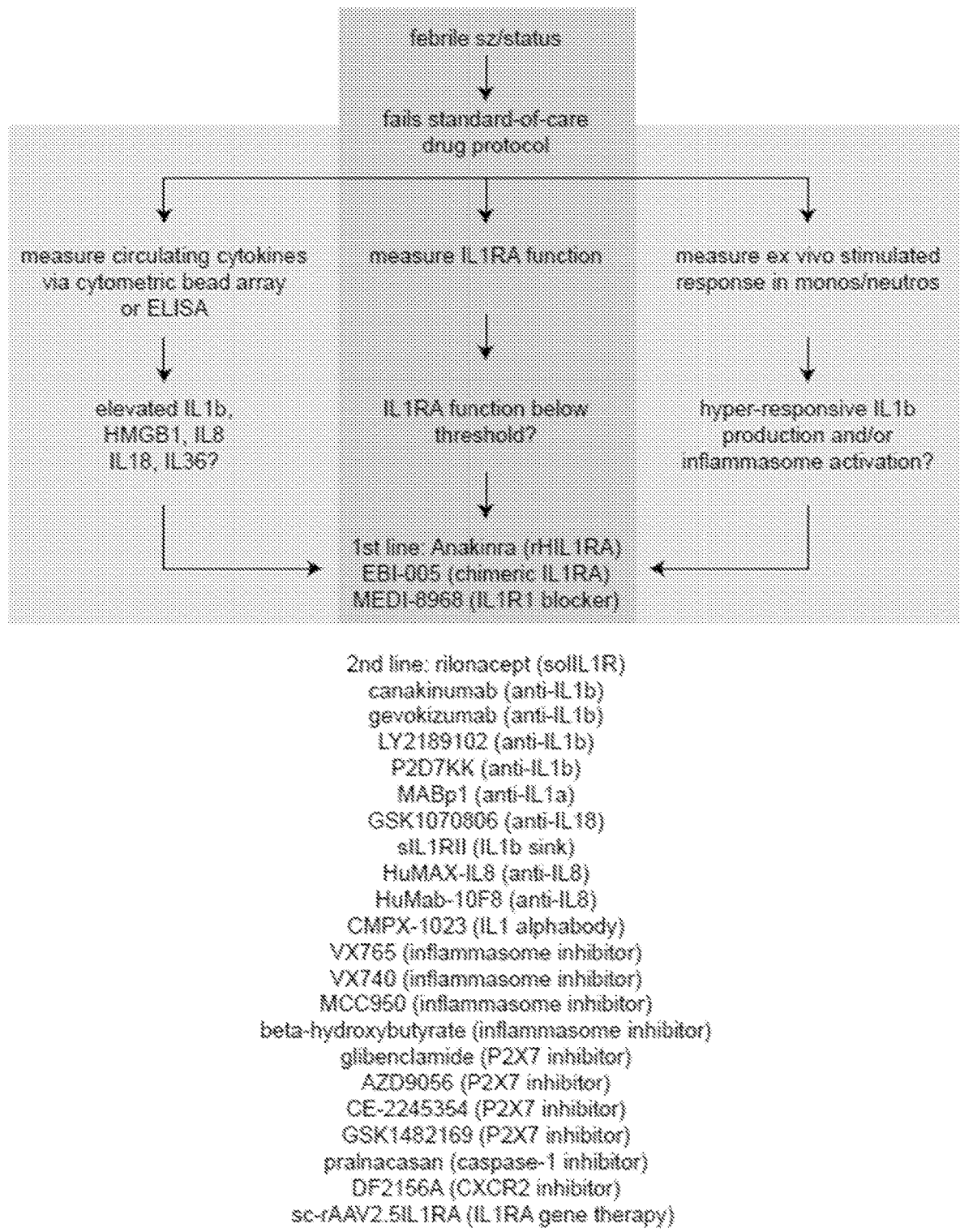

FIG. 9 is a schematic showing an example of a diagnostic scheme for identifying a subject as being a candidate for an IL-1RA based therapy for a seizure disorder.

DETAILED DESCRIPTION

The typical standard of care cascade for a child who has experienced a febrile seizure followed by additional seizures or status epilepticus generally involves first administering benzodiazepines and then, if no response, occurs, either levetiracetam or fosphenytoin. Failure to respond to either of these drugs typically is followed by administration of valproic acid and intravenous (IV) phenobarbital. Failure to respond to these drugs generally escalates to midazolam infusion with increasing dosage, and finally, failure to respond to midazolam results in induction of a barbiturate coma. This entire protocol usually occurs within the first hour after presentation, and represents the standard of care for febrile status epilepticus that has remained essentially unchanged for decades. A child who fails the initial steps of this protocol, in the absence of any other clear etiology (e.g., stroke or trauma) typically undergoes a lumbar puncture for collection of CSF. Blood samples collected upon presentation and again at the time of the lumbar puncture can be submitted for determination of an infectious cause immediately prior to initiation of prophylactic antibiotics. The samples also may be submitted at this point for clinical testing using an autoimmune epilepsy battery.

Anakinra (also known as Kinaret) is recombinantly-produced human IL-1RA, and is a drug that can be used to treat seizure disorders in some patients. For example, some children with FIRES respond to anakinra, as described elsewhere (Kenney-Jung et al., *Ann. Neurol.* 80(6):939-945, 2016). However, many children presenting with FIRES do not respond to anakinra. Likewise, many children who present with seizure disorders that do not fulfill the criteria for FIRES (a much larger population of NICU and PICU cases) may respond to drugs like anakinra, but to date there is no clear path to identifying patients who are likely to respond.

This document provides materials and methods for identifying subjects (e.g., humans or non-human mammals) who are likely to respond to anakinra treatment or other 1L-1RA replacement or supplementation therapies, or other treatments that can attenuate IL-1R inflammatory signaling (e.g., compounds that modulate or antagonize the IL-1β pathway), as well as materials and methods for identifying subjects who are not likely to respond to treatment with such therapies. In some embodiments of the methods provided herein, testing for IL-1RA function and/or IL1RN expression (e.g., to determine the IL-1RA isoform expression pattern) may occur when a CSF sample is tested using an autoimmune epilepsy battery as described above.

The methods provided herein can include assaying a biological sample from a subject to determine the level of IL-1RA protein expression, the level of IL1RN mRNA expression, or the level of IL-1RA activity. Useful biological samples can include, without limitation, serum, serum microvesicles, cerebrospinal fluid (CSF), and cells such as neutrophils, monocytes, peripheral blood mononuclear cells (PBMC), or fibroblasts. Subjects who can be evaluated and treated according to the methods described herein can be humans or non-human mammals (e.g., laboratory animals such as mice and rats; in some cases, such rodents can serve as models for seizure disorders).

In some embodiments, the level of IL-1RA function can be used to guide decisions regarding the use of anakinra or other therapies that can increase IL-1RA function in acutely ill pediatric patients suffering from seizure disorders such as FIRES, DIRA, PASS, or MRE. Other therapies that may be useful in the methods provided herein include, without limitation, one or more of the following: anakinra (available from Swedish Orphan Biovitrum), EBI-005 (chimeric IL-1RA; Eleven Biotherapeutics), MEDI-8968 (IL1R1 blocker; MedImmune), rilonacept (solIL1R; Regeneron), canakinumab (anti-IL-1β; Novartis), gevokizumab (anti-IL-1β; Novartis), LY2189102 (anti-IL-1β; Eli Lilly), P2D7KK (anti-IL-1β), MABp1 (anti-IL1α;)(Biotech), GSK1070806 (anti-IL-18; GlaxoSmithKline), sIL1RII (IL-1β sink), HuMAX-IL8 (anti-IL-8; Genmab), HuMab-10F8 (anti-IL-8; Cormorant Pharmaceuticals), CMPX-1023 (IL-1 alphabody; Copmlix NV), VX765 (inflammasome inhibitor; Vertex Pharmaceuticals), VX740 (inflammasome inhibitor; Vertex Pharmaceuticals), MCC950 (inflammasome inhibitor; Pfizer), beta-hydroxybutyrate (inflammasome inhibitor; Accera), glibenclamide (P2X7 inhibitor; Sanofi-Aventis), AZD9056 (P2X7 inhibitor; AstraZeneca), CE-2245354 (P2X7 inhibitor), GSK1482169 (P2X7 inhibitor; GlaxoSmithKline), pralnacasan (caspase-1 inhibitor; Vertex Pharmaceuticals), DF2156A (CXCR2 inhibitor; Dompe Farmaceutici S.p.A), and sc-rAAV2.5IL-1RA (IL-1RA gene therapy).

Various techniques can be used to assess the level of IL-1RA expression and activity in a subject. For example, the methods provided herein can include measuring the functional activity of IL-1RA, IL-1β, and/or IL-18 (a member of the IL1 family) in serum or CSF using immunological methods (e.g., ELISA) or cytokine bead array assays. In some cases, ex vivo cell-based assays can be used. The IL-1 family cytokines are among the most potently proinflammatory innate immune proteins, and their signaling therefore is tightly regulated by a variety of factors. IL-18 and IL-1β are produced as preforms that are activated only when cleaved by the inflammasome. IL-1β and IL-1a bind to the surface decoy receptor (IL-1RII) with higher affinity than the active receptor (IL-1RI). Conversely, IL-1RA binds with higher affinity to IL-1RI, without causing signal transduction, and it competitively blocks binding of IL-1β and IL-1a. In addition, soluble decoy forms of IL-1RI and IL-1RII are secreted, and can bind and sequester IL-1a and IL-β to prevent signaling. A critical failure in any one of these regulatory components could lead to elevated IL-1R signaling, increasing the chance of a false negative result by single parameter diagnostic measures. Therefore, a cell-based assay can be a useful functional measure of overall IL-1R signaling. For example, as described in the Examples herein, defective IL-1RA activity can be detected in a cell-based reporter assay that tests the ability to block a concentration curve of IL-1β (essentially establishing an $IC_{50}$ for the patient's IL-1RA molecule). Since some subjects who do not respond to anakinra have normal IL-1RA function, this assay may be a useful diagnostic tool for guiding therapy decisions, by rapidly identifying a functional DIRA-like condition.

In some embodiments, methods that include measuring the stimulated release of inflammatory cytokines from neutrophils, monocytes, or PBMCs acutely isolated from subjects with seizure disorders, even after in vitro stimulation periods as short as about 3 hours, can be used to provide insight into inflammatory status and guide therapy decisions. Because the IL-1 family of cytokines is extremely labile in body fluids, detection in patient-derived biospecimens such as serum, plasma, or CSF using traditional techniques such as ELISA or other antibody-based assay methods can be challenging. Determining that a subject has elevated release of IL-1β in neutrophils, monocytes, or PBMCs stimulated with LPS or TNFα, for example, may support the introduction of IL-1RA boosting or IL-1β-targeting therapies.

Neutrophils and monocytes are principal sources of IL-1β. Seizures can be triggered, maintained, or propagated by neutrophil-derived IL-1β in response to diverse stimuli such as peripheral infection, or due to genetic or epigenetic predisposition to neutrophil hyper-responsiveness. In some assay methods, therefore, neutrophils, monocytes, or PBMCs can be acutely isolated from a patient blood sample and primed by exposure to LPS (or another toll-like receptor agonist, or a biological or chemical compound that can drive neutrophil activation) prior to stimulation with a dose range of ATP or another stimulant (e.g., an ATP derivative, a peptide agonists such as N-formylmethionyl-leucyl-phenylalanine (fMLP), or another biological or chemical compound that can drive neutrophil effector function). Under such conditions, neutrophils or monocytes can release IL-1β in an amount that can be readily measured in culture supernatants using methods such as ELISA or cytokine bead array assays. The dose-response curve, normalized to number of neutrophils or monocytes, can be used to calculate a half-maximal effective concentration ($EC_{50}$) for ATP stimulated IL-1β release from the patient's cells. By comparison to the $EC_{50}$ from corresponding healthy controls, a patient can be categorized as "normal" (e.g., when the patient's $EC_{50}$ is within one standard deviation of the healthy control $EC_{50}$, less than a z-score or effect size of 1.0, indicating an IL-1β response similar to 84% of the healthy population), "abnormal" (e.g., when the patient's $EC_{50}$ is within 1 to 2 standard deviations above the healthy control $EC_{50}$, less than a z-score or effect size of 2.0, indicating an IL-1β response similar to 98% of the healthy population), or "hyper-responsive" (e.g., when the patient's $EC_{50}$ is greater than 2 standard deviations above the healthy control $EC_{50}$, greater than a z-score or effect size of 2.0, indicating an IL-1β response that exceeds that of 98% of the healthy population). Characterization of a patient as "hyper-responsive" can justify administration of drugs such as anakinra to reduce or ameliorate seizures, while characterization as "normal" or "abnormal" can indicate that the patient is not a good candidate for IL-1RA or IL-1β based therapy, and that a different approach should be used.

It is noted that, in addition to IL-1β, inflammatory responses that may be indicative of inflammamodulatory therapy can include other ligands of the IL-1 receptor, such as IL-1a and IL-1RA, as well as members of the IL-1 superfamily such as IL-18, IL-33, IL-36, IL-37, and IL-38. Thus, these markers also can be measured to assess whether a subject can be identified as likely to respond to immunomodulatory therapy such as anakinra. Further, alternative effect size ranges may be employed as evidence of anakinra efficacy builds; likewise, alternative effect size ranges may be warranted for different age groups, such as neonates, infants, children, adolescents, young adults, adults, and the elderly. For patients with periodic seizure syndromes, assessment of neutrophil hyper-responsiveness can be used during remission phase to predict impending relapse. For example, the IL-1β release $EC_{50}$ can be measured regularly over an interval of time, and a shift in the $EC_{50}$ indicating increased neutrophil responsiveness can be used to initiate therapy aimed at preventing relapse. Alternative readouts of neutrophil hyper-responsiveness can include flow cytometric assessment of surface markers that indicate activation status, such as increased CD66b, increased CD88, or decreased CD62L. The degree of activation can be measured by establishing a mean fluorescence intensity (MFI) for these surface markers on neutrophils or monocytes from healthy subjects and comparing the MFI from seizure patients.

In some cases, neutrophils, monocytes, or PBMCs acutely isolated from a subject can be primed and stimulated, and treated with a candidate drug to evaluate the cellular response to the drug. For example, neutrophils from a FIRES patient can be primed (e.g., with LPS), treated with anakinra or another drug (e.g., another inflammamodulatory drug), stimulated (e.g., with ATP), and then evaluated for release of IL-1β or IL-1R ligand or IL-1 superfamily member. By comparing the release with and without the test drug, the likelihood of the patient's response to the drug can be determined.

In some cases, an IL-1RA functional test can be employed to generate an antagonism index for the subjects endogenous IL-1RA, both in serum and CSF (although serum alone may be adequate if necessary, based on availability of material). The antagonism index can be compared to a control range of antagonistic function measured in healthy subjects, such that the healthy control range can be used to determine a threshold for a "normal" antagonism index. Values below the threshold can result in identification of the subject as likely to respond to recombinant IL-1RA (anakinra) as a therapeutic intervention. For example, a child with 50% of the functional antagonism of "normal" IL-1RA may not be likely to benefit substantially from anakinra, but a child with 10% or 1% of the functional antagonism may show a profound benefit from supplementation with the recombinant antagonist. Thus, the in vitro antagonism index can provide a diagnostic marker for use of a drug such as anakinra or adjunct therapies. The use of such diagnostic strategies can accelerate the time to use of anakinra or another IL-1RA based therapy, thereby reducing the brain injury that can accrue with time in status epilepticus and/or drug-induced coma. The diagnostic methods provided herein also can aide in guiding therapy decisions away from the IL-1β pathway when the antagonism index is normal, accelerating the use of alternative agents targeting other inflammatory pathways.

In some embodiments, methods for determining IL-1RA activity based on an antagonism index can include measuring binding displacement of fluorescently conjugated IL-1β to derivatized beads (also fluorescent, but in another channel) having IL-1R covalently conjugated to their surface. In some cases, for example, binding displacement assays can include immunoprecipitating endogenous IL-1β in a patient's sample on beads conjugated with anti-IL-1β antibodies. The IL-1β-depleted sample can be incubated with IL-1R beads in the presence of labeled IL-1β at $EC_{90}$ (enough IL-1β to saturate 90% of the binding sites). A displacement index then can be calculated for the patient and compared to healthy control ranges. Such methods also can be translated into a chip-based system using absorbance or fluorescence and IL-1R bound to the detector surface, again measuring displacement of labeled IL-1β.

Somewhat similar to the above methods, another strategy for assessing IL-1RA function can include measuring displacement of IL-1β binding from a molecularly imprinted polymer (MIP). Such methods can utilize, for example, an electrically conductive MIP that binds IL-1β (mimicking IL-1R binding), where the MIP-IL-1β complex serves a substrate for screening patient IL-1RA displacement. In some cases, the MIP-based methods can include a fluorescent assay instead of an electrical assay, or can be bead-based via flow cytometry.

In some embodiments of the methods provided herein, portions of IL-1 family genes in a subject can be sequenced (e.g., using rapid RNA-seq based targeted exon sequencing or another suitable method) to determine whether the subject has IL-1 polymorphisms that may be associated with functional impairment or altered expression of key isoforms. As described in the Examples, for example, a pediatric patient with deficient IL-1RA function showed elevated levels of IL-1RA protein in CSF, indicating that absolute expression of IL-1RA is insufficient to determine a deficiency in function. Sequencing analysis in this patient revealed markedly reduced expression of the principal intracellular isoforms of IL-1RA (isoforms 2 and 3, which are the acute response isoforms of the protein), which were verified by protein analysis of lysates from the patient's PBMCs. Thus, sequence-based methods also can be used in the methods provided herein for identifying subjects as being likely or not likely to respond to IL-1RA related therapies. In some cases, sequencing methods can be used to establish a pattern of mutations within intronic regions that is consistent with possible splice site acceptor-donor defects. Alternatively or at the same time, RNAseq or ChIPseq can be used to characterize isoform expression patterns and/or splicing defects. In the index case described in the Examples herein, a chain of possible SNPs has been identified in the intron between exons 3 and 4, within a possible splice controller region near the start of exon 4. Several of these SNPs have not been previously characterized or published.

In some cases, surface plasmon resonance (SPR) can be used to measure binding affinity of patient-specific IL-1RA, since some functional deficiencies can result from reduced binding affinity or receptor on-off times. SPR can provide a reasonably high-throughput, highly quantitative method for assaying IL-1RA antagonism to detect binding on IL-1R either adhered to a detector surface or expressed on membranes that have been disrupted into sheets and adhered to the detector surface. This method may be used with a chip-based sensor or diagnostic SPR device, for example. As with the HEK-based functional assay, a binding index (e.g., affinity) can be calculated and compared to healthy control ranges.

In some embodiments, an assay for determining IL-1RA function can include using a commercially available sensing technology such as the Octet series offered by ForteBio. This can involve using a bio-layer interferometry that is similar in concept to SPR and can have similar sensitivity but a much higher throughput.

As described herein, this document provides methods that can be used to identify subjects with seizure disorders as being likely to respond to treatment with a therapy that can reduce IL-1R inflammatory signaling (e.g., anakinra). In some cases, the methods can include determining that a subject with a seizure disorder has decreased IL-1RA function as compared to a control level of IL-1RA function (e.g., the level of IL-1RA function in one or more normal subjects who do not have a seizure disorder). It is to be understood that a control level of IL-1RA function, as used herein, typically is determined using the same method used to determine the level of IL-1RA function in the subject having the seizure disorder. This document discloses multiple methods that can be used to assess IL-1RA function; any of these can be used to identify a subject as being likely to respond to treatment with anakinra or another therapeutic that reduces IL-1R inflammatory signaling. As used herein, a "decrease" in in IL-1RA function refers is a level of IL-1RA function that is lower (e.g., at least 5% lower, at least 10% lower, at least 25% lower, at least 50% lower, at least 75% lower, at least 90% lower, or at least 95% lower) than a corresponding control level of IL-1RA function. In some cases, a decrease in IL-1RA function can be a decrease in functional IL-1RA antagonism below a predetermined threshold level of functional IL-1RA antagonism. The threshold can be, for example, a level of functional IL-1RA antagonism that is 50% or less (e.g., 25% or less, 10% or less, or 5% or less) than a corresponding control level of functional IL-1RA antagonism.

In some cases, however, as described herein, a reduction in IL-1RA function can be indicated by an increased inflammatory response in a subject. The inflammatory response can be increased by at least 5% (e.g., at least 10%, at least 25%, or at least 50%) as compared to a corresponding control inflammatory response observed for subjects who do not have the seizure disorder. In some embodiments, in increased inflammatory response can be at least two (e.g., at least 2.5, at least 3, or at least 4) standard deviations higher than the corresponding control inflammatory response. Further, in some cases, the methods provided herein can include measuring the relative amounts of IL-1RA isoforms in a sample from a subject with a seizure disorder, and determining that the subject has a ratio of soluble IL-1RA (including isoforms 1 and 4/5) to intracellular IL-1RA (including isoforms 2 and 3) that is increased relative to a control ratio of soluble IL-1RA:intracellular IL-1RA. The ratio can be increased by at least 5% (e.g., at least 10%, at least 25%, or at least 50%) as compared to a corresponding control ratio of soluble IL-1RA:intracellular IL-1RA.

Once a subject with a seizure disorder is identified as being likely to respond to treatment that attenuates IL-1R inflammatory signaling, using the methods disclosed herein, the subject can be treated with, for example, anakinra or another IL-1RA replacement therapy, an IL-1RA supplementation therapy, or another therapy that reduces inflammatory signaling via IL-1R.

The methods described herein also can be used to identify a subject (e.g., a human or a non-human mammal) as being at risk for experiencing a seizure disorder. For example, IL-1RA function can be assessed in the subject using a method as described herein, and if the level of IL-1RA function is decreased as compared to a corresponding control level of IL-1RA function, the subject can be identified as having an increased likelihood of experiencing a seizure disorder.

In addition, the methods provided herein can be used as part of a diagnostic protocol for identifying subjects who may respond to IL-1RA-based therapies or other therapies for treatment of seizure disorders. As depicted in FIG. 9, for example, IL-1RA function can be assessed using one or more of the methods described herein and, based on the assessment, a treatment strategy can be indicated.

The invention will be further described in the following examples, which do not limit the scope of the invention described in the claims.

EXAMPLES

Example 1—Materials and Methods

Patient samples: Samples from patients with normal pressure hydrocephalus (NPH), focal epilepsy, Landau-Kleffner Syndrome/electrical status epilepticus in sleep (ESES), or FIRES were obtained from the Mayo Clinic Neuroimmunology Laboratory. Healthy control serum or PBMCs were obtained directly from consenting volunteers.

IL-1RA enzyme-linked immunosorbent assay: The human IL-1RA/IL1F3 Quantikine ELISA kit (R&D Systems) was used according to the manufacturer's instructions. Serum and CSF samples were diluted (1:2-1:5000 in assay diluent) and duplicate samples were measured against a standard curve (31.3-2000 pg/mL in duplicate). After chromogen development, absorbance was measured on a Spectramax M3 multi-mode microplate reader (Molecular Devices). Absorbances falling outside the range of the standard curve were reanalyzed at different dilutions.

Cytometric bead assay: The BD CBA human inflammatory cytokine Kit, BD CBA human chemokine kit, and BD CBA human enhanced sensitivity IL-1β flex set (BD Biosciences) were used according to the manufacturer's instructions. Clarified cell supernatants were diluted 1:2-1:10 in assay diluent and were measured against a standard curve. Briefly, supernatants were incubated in the dark with capture beads and detection reagent for 2-3 hours at room temperature. Beads were washed and then acquired on a BD Accuri C6 (BD Biosciences) flow cytometer equipped with a 488 nm laser (filter set: 533/30, 585/40, 670LP) and a 640 nm laser (filter set: 675/25, 780/60). Data were analyzed in FCAP Array Software (BD Biosciences).

HEK-Blue IL1R cells: Human embryonic kidney (HEK) cells expressing murine and human IL-1 receptor proteins, as well as expressing secreted embryonic alkaline phosphatase under NF-kB/AP1 transcriptional control (HEK-Blue IL1R, InvivoGen), were maintained in DMEM with 10% FBS, 2 mM glutamine, 50 U/mL penicillin, 50 µg/ml streptomycin, 100 µg/ml Normocin, 200 µg/mL hygromicin B, 1 µg/mL puromycin, and 100 µg/ml Zeocin. Heat inactivated human serum tested negative for background alkaline phosphatase activity. In initial experiments, HEK-Blue IL1R cells were treated for 24 hours with 0-100 ng/mL recombinant human IL-1β (Peprotech) in the presence of 0-200 ng/mL anakinra. In subsequent experiments, cells were treated with 32 pg/mL IL-1β for all conditions. After 3 hours, saturating concentrations (10 µg/mL) of anakinra were added to the cells to block further IL-1R signaling, and endpoint supernatants were collected at 24 hours. Supernatants (20-40 µL) were mixed with prewarmed QUANTI-Blue reagent (160 µL, InvivoGen) and incubated at 37° C. in a Spectramax M3 multi-mode microplate reader (Molecular Devices). Absorbance at 655 nm was recorded every 5 minutes for 3 hours via kinetic read. The basal absorbance of untreated HEK-Blue IL-1R cell supernatant was subtracted from all samples to normalize for non-specific signal.

Real-time polymerase chain reaction: All lysate samples were stored at −80° C. in 1% β-mercaptoethanol in Buffer RLT Plus (Qiagen) prior to disruption and homogenization with QIAShredder columns (Qiagen), and RNA isolation using the RNeasy Plus Micro Kit (Qiagen). RNA concentration was estimated with a NanoDrop spectrophotometer (ThermoFisher). The Transcriptor First Strand cDNA Synthesis kit (Roche) was used to synthesize cDNA from RNA samples using oligo-dT primers to target mRNA. Equal amounts of sample template RNA were used for each cDNA reaction. The reactions were placed in a thermal block cycler and incubated at 55° C. for 45 minutes, and then inactivated by heating at 85° C. for 5 minutes. Samples were diluted with PCR grade water (1:10-1:50) and stored at −20° C. RT-PCR was performed according to the protocol outlined with SsoAdvanced Universal SYBR Green Supermix (Bio-Rad) and each sample was run in triplicate. Briefly, 20 µL reactions were prepared by adding 10 µL of SsoAdvanced universal SYBR Green 2× master, 2 µL each of 5 forward and 5 µM reverse primers (total 4 µL), 1 µL nuclease-free water, and 5 µl sample template containing 2-10 ng cDNA. Samples were run on a Bio-Rad CFX Connect system for 50 cycles with the following protocol: 15 seconds at 95° C., 45 seconds at 55° C., and 5 seconds at 65° C. Primers (TABLE 1) were selected using Primer BLAST (NCBI) to have melt temperatures around 60° C. Melt curve analysis was used to determine specificity of each reaction. Data were exported and analyzed in excel using the Pfaffl method to determine relative quantitation based on an estimated amplification efficiency of 95%. Expression across all samples was normalized to the GAPDH housekeeping gene.

IL-1RN Sanger sequencing: IL-1RN gene segment amplicons were generated from FIRES patient DNA by PCR using Phusion High-Fidelity DNA polymerase (New England Biosciences) and primers targeting ~4000 bp segments of IL-1RN (TABLE 2). Thermocycling conditions followed manufacturer recommendations, with a 2 minute elongation step for each of 35 cycles. Amplicons were extracted from agarose gels following electrophoresis using the Qiaquick Gel Extraction Kit (Qiagen). Targeted long read Sanger sequencing was performed on extracted amplicons by the Mayo Clinic Gene Expression Core facility and by Genewiz using amplicon specific sequencing primers (TABLE 2). Trace data were analyzed and aligned with Mutation Surveyor software and confirmed variants were compared to NG 021240.1 RefSeqGen cited variants (available at www.ncbi.nlm.nih.gov/gene/3557).

Statistical analyses: $\alpha=0.05$ and $\beta=0.2$ were established a priori. Post hoc power analysis was performed for all experiments and significance was only considered when power was ≥0.8. Normality was determined by the Shapiro-Wilk test or the Kolmogorov-Smirnov test. For multiple comparisons, one-way analysis of variance (ANOVA) or non-parametric (Kruskal-Wallis) tests were performed where appropriate. Reported P values were corrected for multiple comparisons (Holm-Sidak correction for ANOVA; Dunn's correction for Kruskal-Wallis). Unpaired two-tailed Student's t-tests were used for comparisons made between two groups. Curran-Everett guidelines were followed.

Figure 1A:
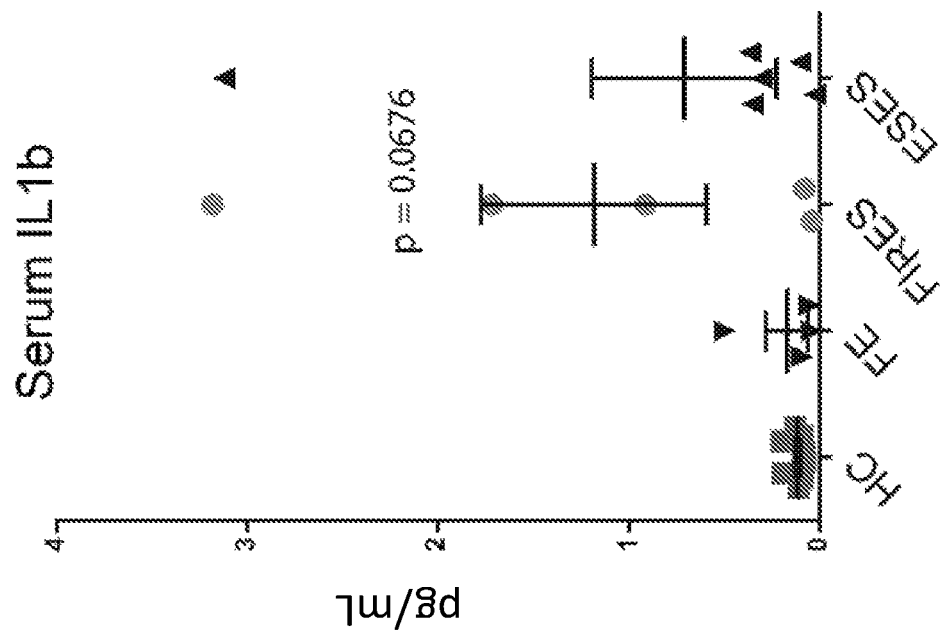
FIGS. 1A-1D are a series of graphs plotting serum and CSF levels of IL-1RA and IL-1β in for subjects with FIRES and other seizure disorders.
Figure 1B:
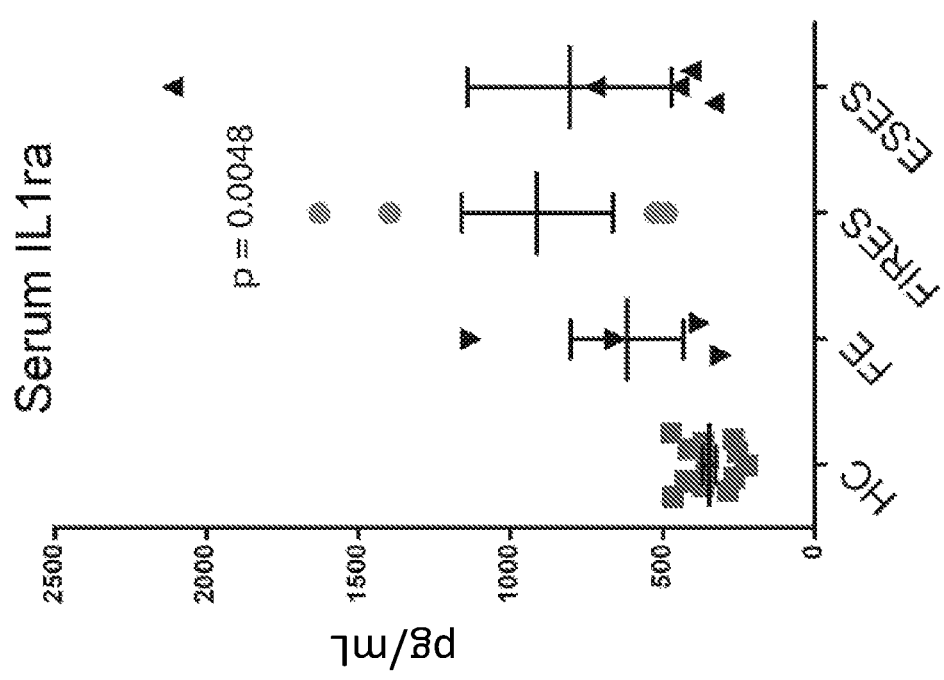
Figure 1C:
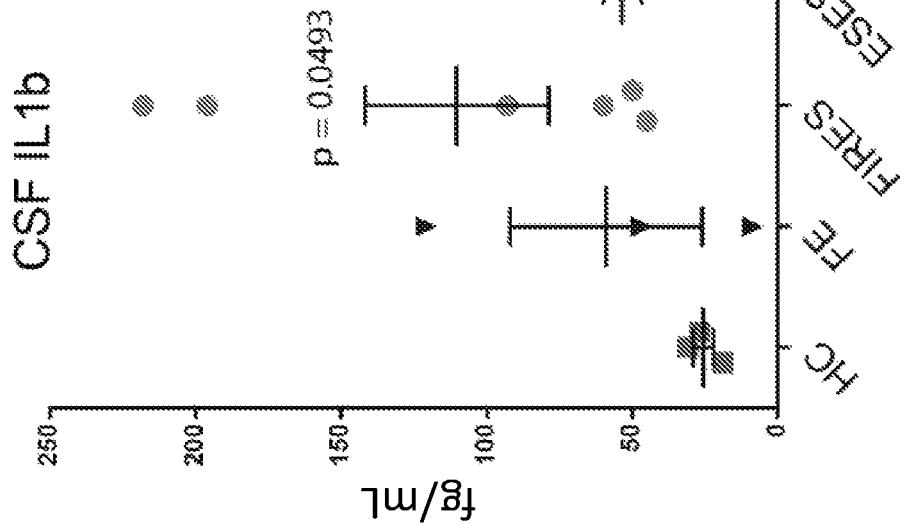
Figure 1D:
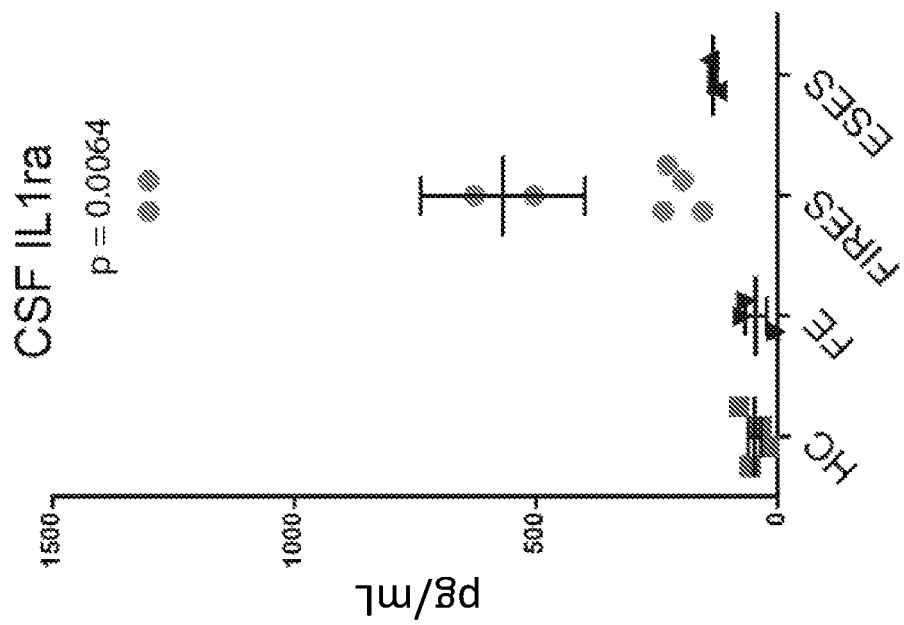

Example 2—Elevated IL-1RA in Serum and IL-1β and IL-1RA in CSF of FIRES Patients To determine whether there was a diminished level of endogenous IL-1RA in FIRES patient serum or CSF, IL-1RA levels were measured by enzyme-linked immunosorbent assay (ELISA) in FIRES patient serum and CSF before and after initiation of anakinra treatment, as well as in serum from healthy controls, CSF from normal pressure hydrocephalus patients, and serum and CSF from patients with other seizure disorders. Surprisingly, it was observed that prior to anakinra therapy, IL-1RA (FIG. 1A) and IL-1β (FIG. 1B) were marginally elevated in FIRES serum as compared to healthy controls. IL-1RA was strongly elevated in FIRES CSF compared to normal pressure hydrocephalus controls and patients with ESES or focal epilepsy (FIG. 1C). CSF IL-1β levels, which were only rarely detectable in healthy controls, were also elevated in among FIRES patients (FIG. 1D). Serum levels of IL-1RA did not differ between FIRES patients and other chronic seizure patients (FIG. 1A). In several cases, IL-1RA levels in CSF exceeded serum levels in FIRES, suggesting predominant CNS production. This finding also was consistent with reports of elevated IL-1RA following seizure activity (Lehtimaki et al., *Neuroimmunomodulation* 17(1):19-22, 2010). Following anakinra treatment, both serum and CSF levels of IL-1RA were further increased, reflecting detection of the exogenous IL-1RA.

Figure 2B:
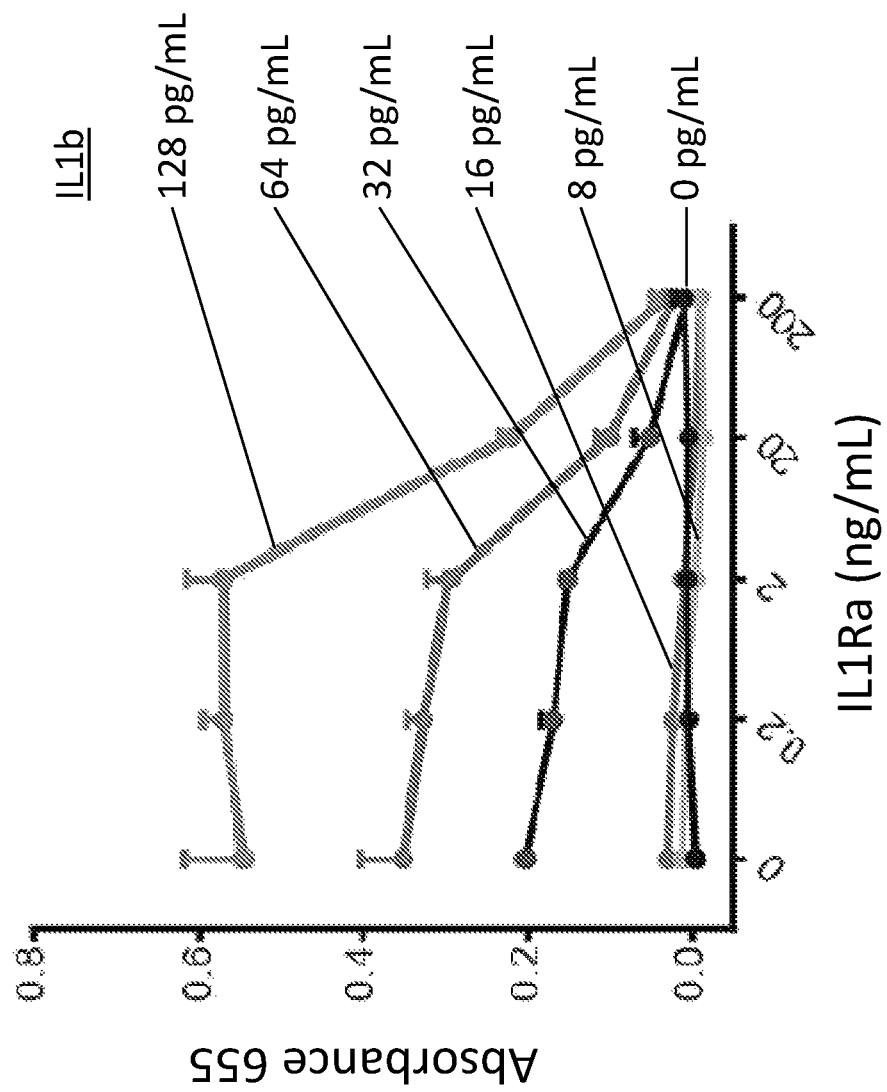
Figure 2C:
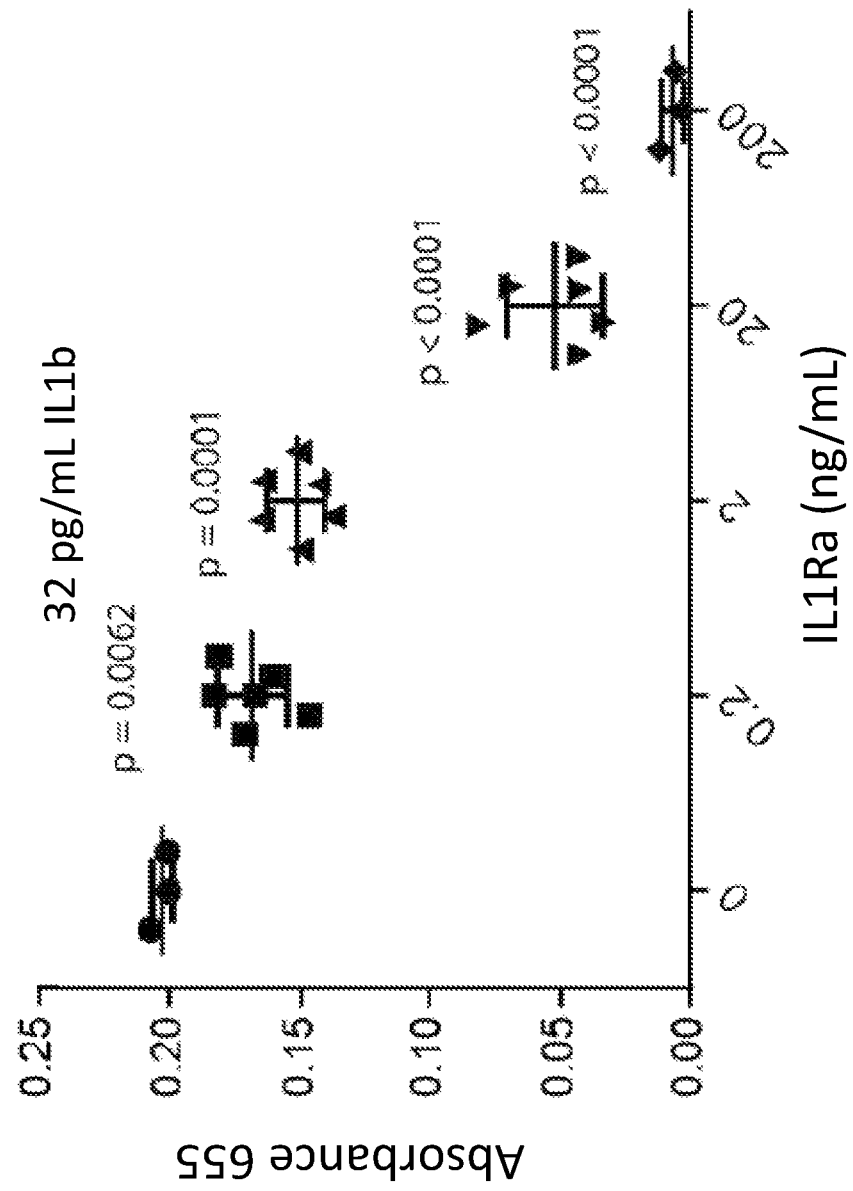

Example 3—A Sensitive Cell-Based Assay for Measuring Serum IL-1R Signaling Activity Given that both IL-1β and IL-1RA were elevated in FIRES patient serum, experiments were conducted to determine whether the elevation translated into a change in overall IL-1R signaling activity. To develop a sensitive functional measurement of IL-1R signaling activity, a cell based assay using HEK-Blue IL1R cells was developed and optimized. These cells express human IL-1R and respond to IL-1R signaling-induced NFκB activity by producing secreted embryonic alkaline phosphatase (SEAP), which dose-dependently results in increased absorbance of 655 nm wavelength light upon incubation with Quanti-Blue substrate (FIG. 2A). Further, this effect can be competitively blocked by co-treatment with recombinant IL-1RA (FIG. 2B). Titration showed that dose of 32 pg/mL IL-1β was most sensitive to blockade by IL-1RA while still retaining sufficient signal-to-noise ratio to limit intra-assay variability (FIG. 2C). Quenching HEK-Blue IL1R cells two hours after treatment, by applying excess IL-1RA, further increased sensitivity of the assay (FIG. 2D).

Example 4—Elevated IL1R Signaling Activity of FIRES Patient Serum

Figure 3B:
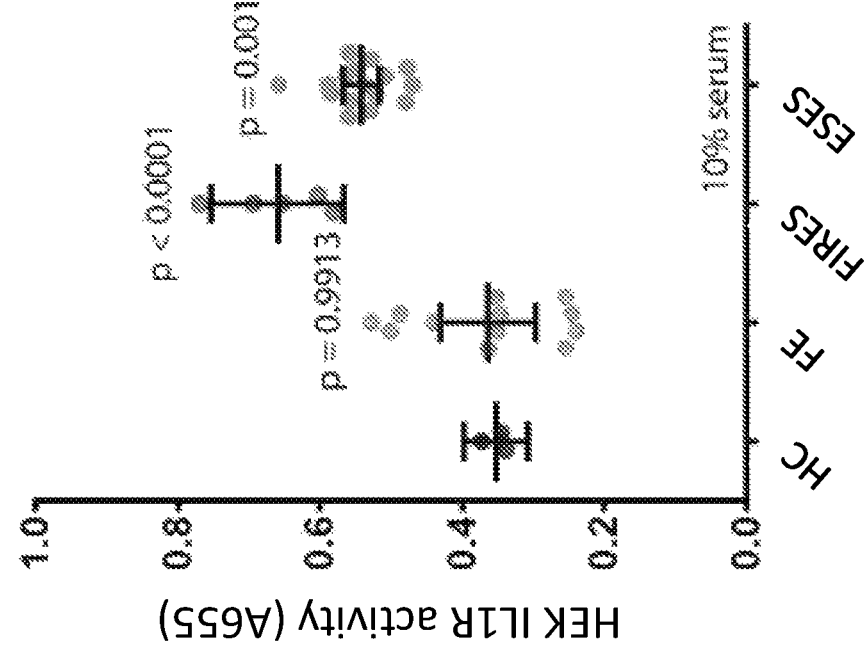
FIGS. 3A-3E are a series of graphs plotting IL-1R signaling activity of serum in FIRES and other seizure disorders. In all experiments, HEK-Blue IL1R supernatants were collected 24 hours after treatment, and were mixed with prewarmed Quanti-Blue detection reagent. Absorption at 655 nm was read after 3 hours. Background absorbance values have been subtracted from all panels.
Figure 3A:
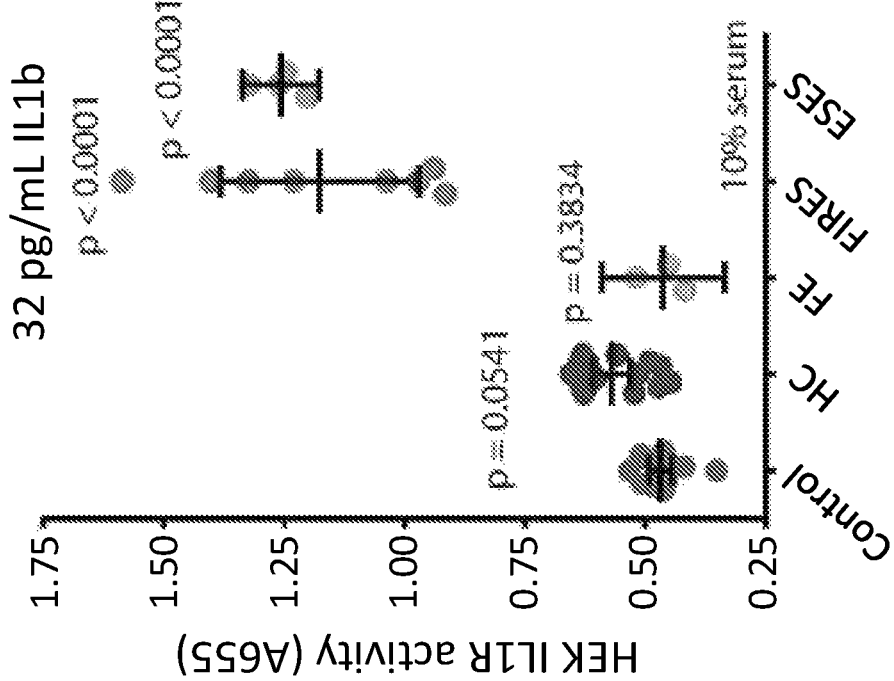
Figure 3D:
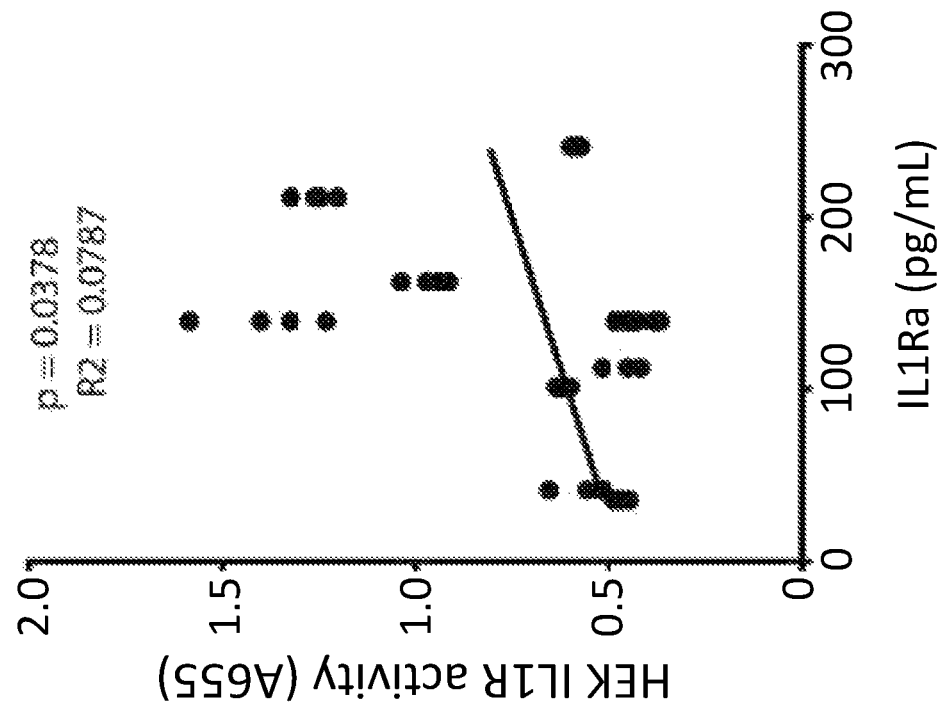
Figure 3C:
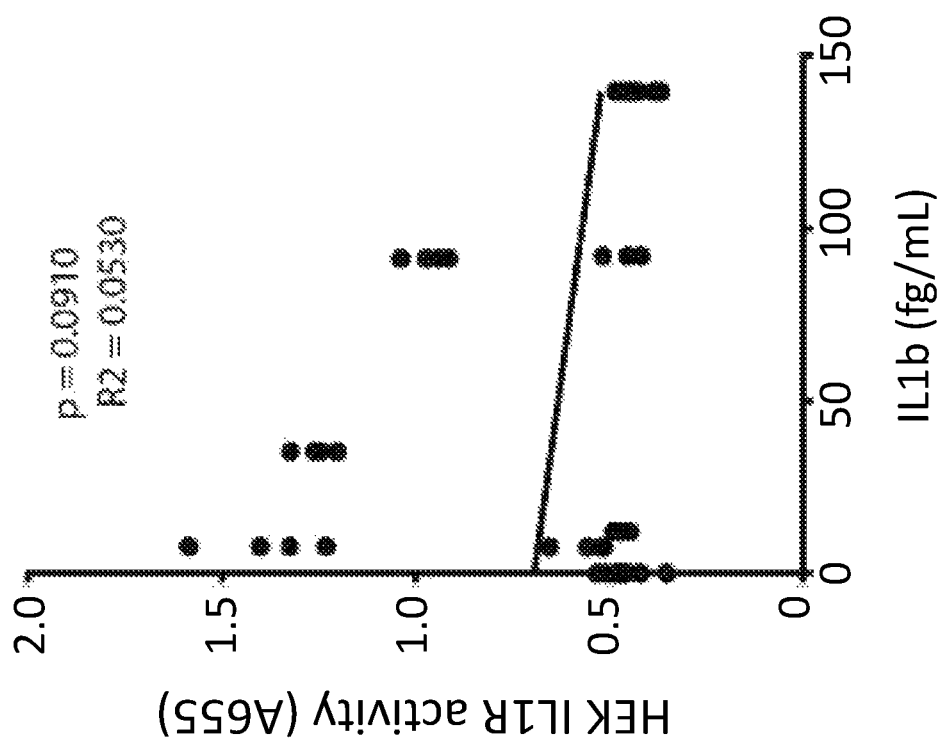
Figure 3E:
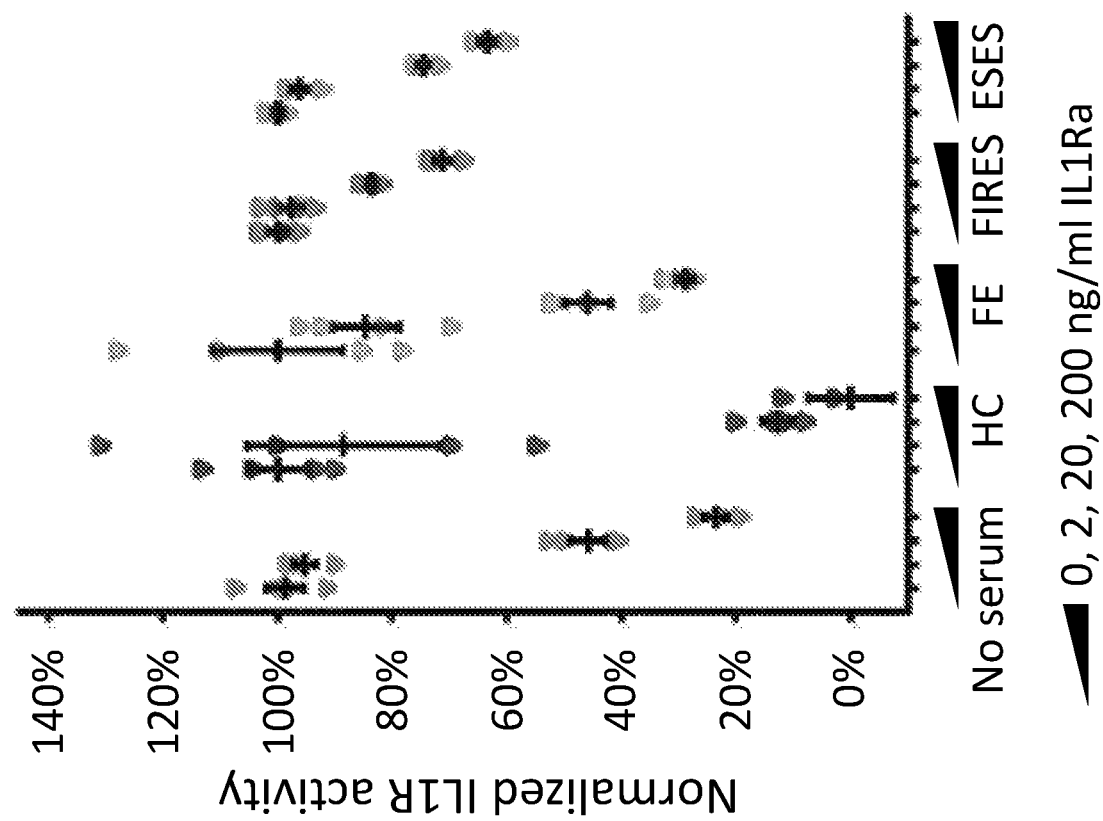

The assay described above was used to measure the endogenous IL-1R signaling activity of serum from healthy controls, and from patients with focal epilepsy, ESES, or FIRES (FIG. 3A). Both FIRES and ESES patients exhibited elevated serum IL-1R activity relative to healthy controls or patients with focal epilepsy, who did not differ from controls. Next, studies were conducted to measure how patient serum modified IL-1R activity in response to a known concentration of IL-1β (FIG. 3B). Surprisingly, FIRES and ESES patient serum synergized with exogenous IL-1β, resulting in a difference in IL-1R activity between cells treated with IL-1β plus FIRES patient serum and cells treated with IL-1β plus healthy control serum that was greater than the difference measured between cells treated with FIRES patient serum alone and healthy control serum alone. Given that the measured concentration of serum IL-1β in these patients was far below the 32 pg/mL used in the assay, the multiplicative increase in IL-1R activity suggested that other serum factors may be driving IL-1R activity, or that a larger reservoir of the serum IL-1β remained undetected by ELISA—possibly because it may be present in microvesicles as described elsewhere (Lopez-Castejon and Brough, *Cytokine Growth Factor Rev* 22(4): 189-195, 2011). Indeed, serum IL-1β levels did not strongly correlate with measured IL-1R activity across all patients (FIG. 3C). Additionally, contrary to expectation, IL-1RA levels correlated with assayed IL-1R activity (FIG. 3D), suggesting that serum factors may be affecting the inhibitory capacity of IL-1RA and causing it to function as an IL-1R agonist rather than an IL-1R antagonist in this assay. This notion was rejected in follow up studies confirming that, in all conditions, the measured increase in IL-1R activity was at least partially suppressed by the addition of exogenous rIL-1RA (FIG. 3E). Serum-elicited IL-1R signaling activity was not completely suppressed by exogenous IL-1RA, indicating that a portion of serum IL-1R ligands may have bound to IL-1R in compartments that were not accessible to exogenously added rIL-1RA. This would be consistent with the presence of IL-1β in serum microvesicles. These findings suggested that, while informative, serum measures of IL-1β and IL-1RA alone or together may represent an incomplete picture of serum IL-1R activity, which may be more accurately gauged by functional cell based assays.

Example 5—Reduced Functional Blockade of IL-1R Signaling by Endogenous IL-1RA in an Anakinra-Responsive FIRES Patient It is likely that the concentration of IL-1RA at the site of production in the brain interstitial space—and by extension, its relevant functional activity—far exceeds the levels detected in serum or CSF. IL-1RA is a downstream transcriptional target of IL-1R signaling and a principle mechanism of negative feedback. Therefore, elevated levels of CSF IL-1RA may represent either a normal protective response to terminate CNS IL-1R signaling in the acute setting, or the continuation of a failed termination of IL-1R signaling in the chronic setting. The fact that the levels of IL-1RA detected in the CSF of an anakinra-responsive FIRES patient represent concentrations of IL-1RA that are sufficient to cause suppression of IL-1R signaling (see, e.g., McIntyre et al., *J Exp Med* 173(4):931-939, 1991; Greenfeder et al., *J Biol Chem* 270(38):22460-22466, 1995; and Hou et al., *Proc Natl Acad Sci USA* 110(10):3913-3918, 2013) suggested the possibility of a dysfunctional IL-1RA protein and failed IL-1R signaling termination.

Figure 4A:
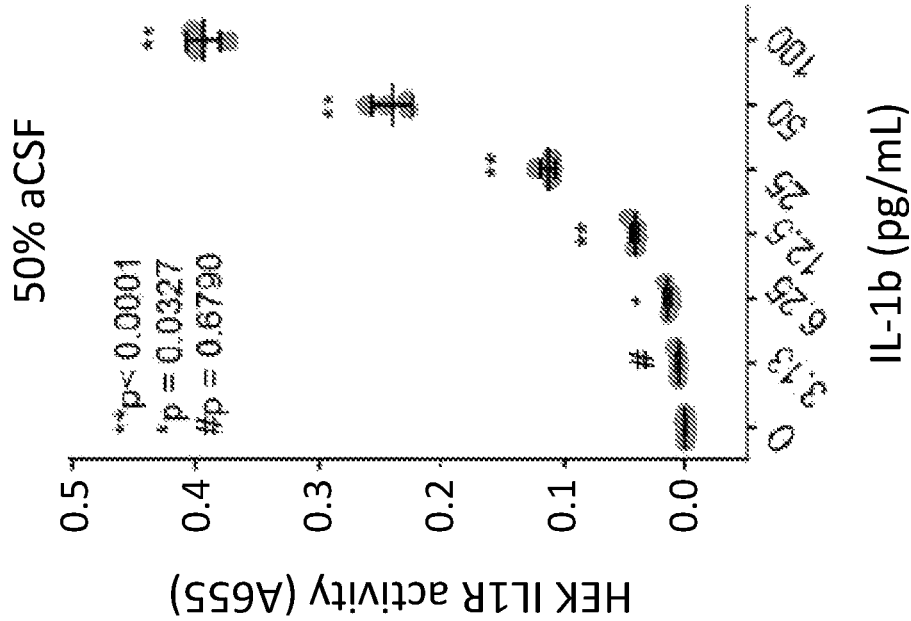
FIGS. 4A-4D are a series of graphs plotting optimization of an IL-1R signaling cell-based functional assay in 50% CSF for measuring IL-1R antagonism by patient IL-1RA. In all experiments, HEK-Blue IL1R supernatants were collected 24 hours after treatment and mixed with prewarmed Quanti-Blue detection reagent. Absorption at 655 nm was read after 3 hours. Background absorbance values have been subtracted from all panels. HEK-Blue IL1R cells were treated with the indicated doses of IL-1β in normal HEK media containing 10% fetal bovine serum (FIG. 4A), serum free media (not shown), or normal HEK media mixed with a 50% solution of artificial cerebrospinal fluid (aCSF.
Figure 4B:
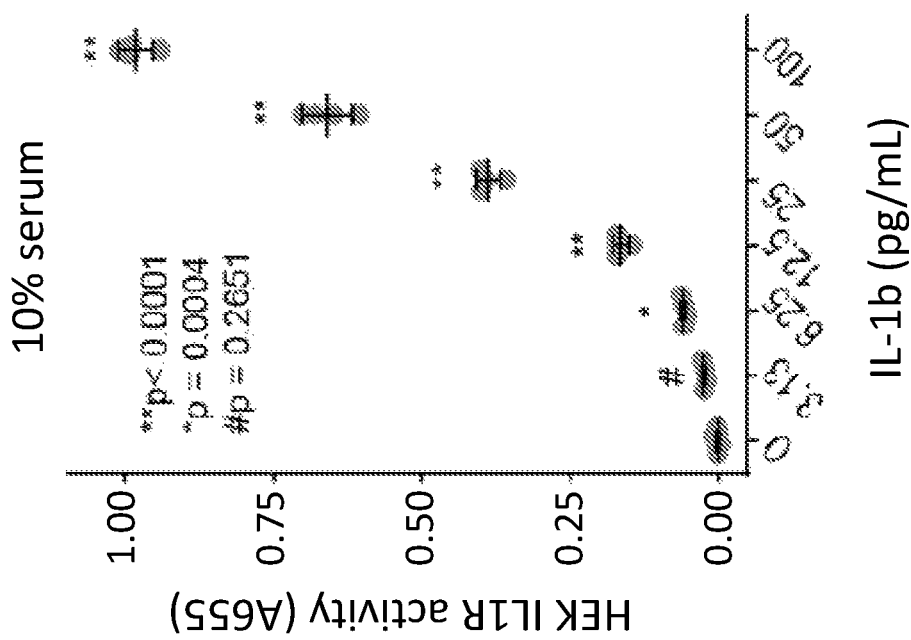
Figure 4C:
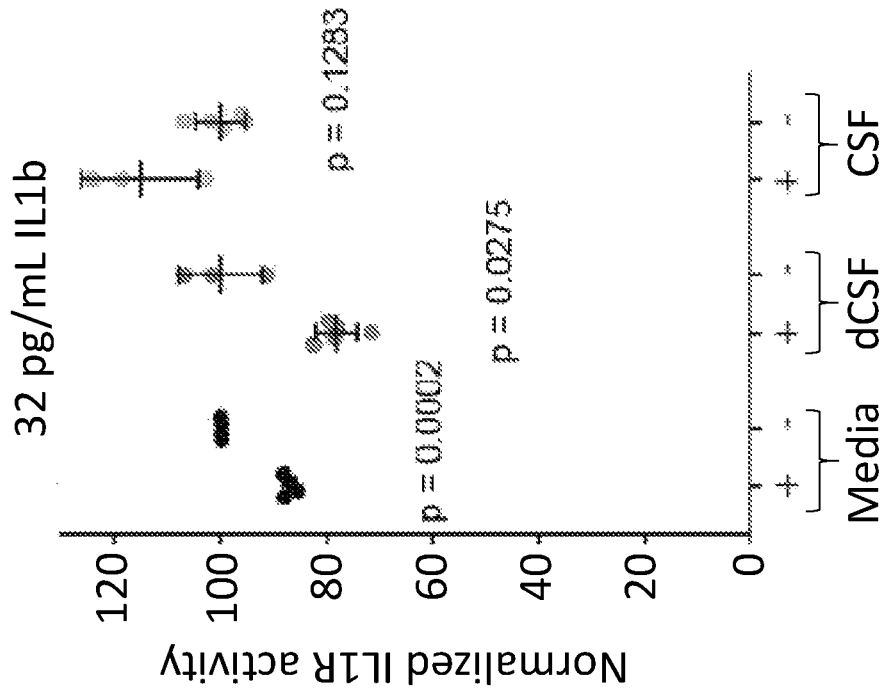
Figure 4D:
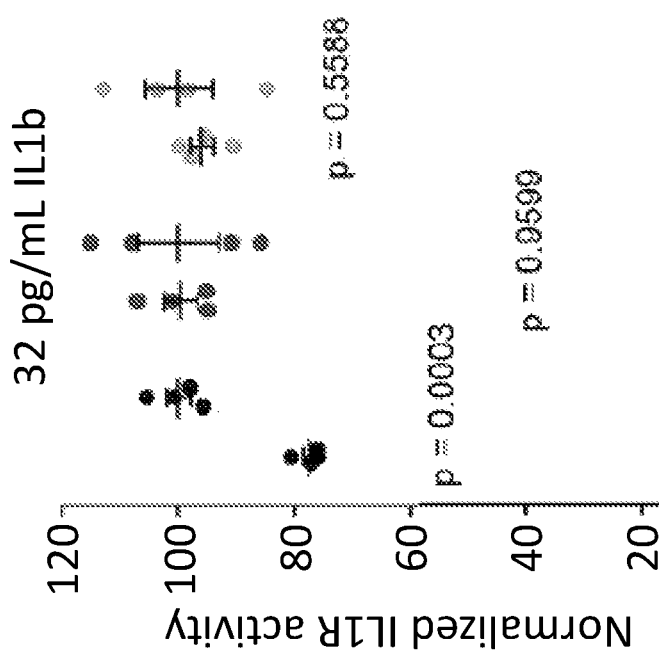
Figure 5C:
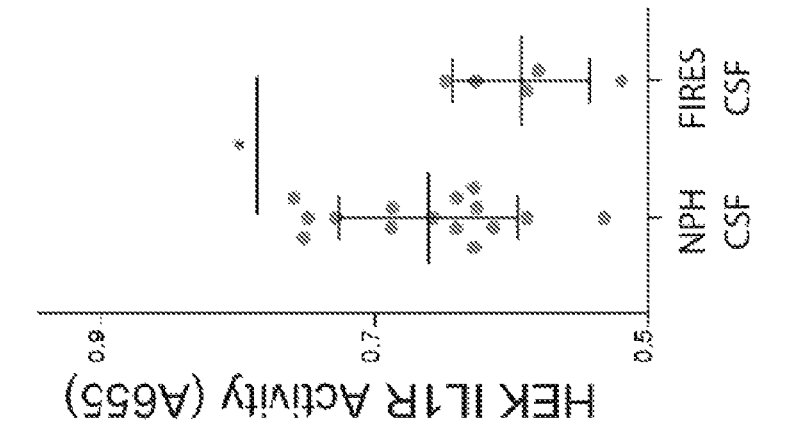
FIGS. 5A-5C are a series of graphs showing that FIRES patient IL-1RA exhibits deficient IL-1R antagonism. In all experiments, HEK-Blue IL1R supernatants were collected 24 hours after treatment, and were mixed with prewarmed Quanti Blue detection reagent. Absorption at 655 nm was read after 3 hours.
Figure 5B:
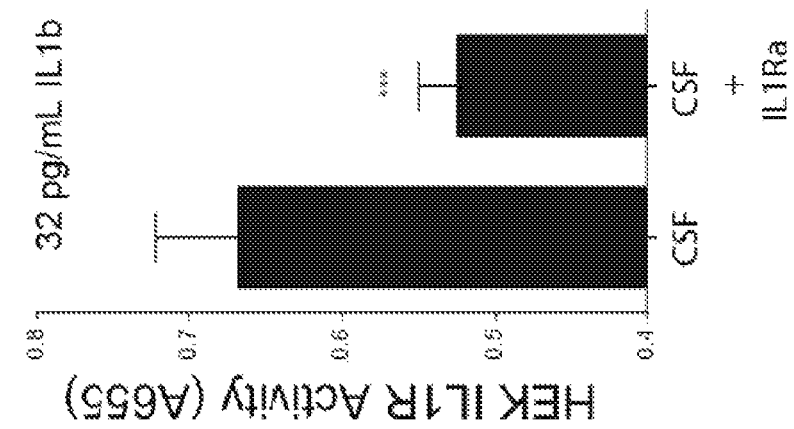
Figure 5A:
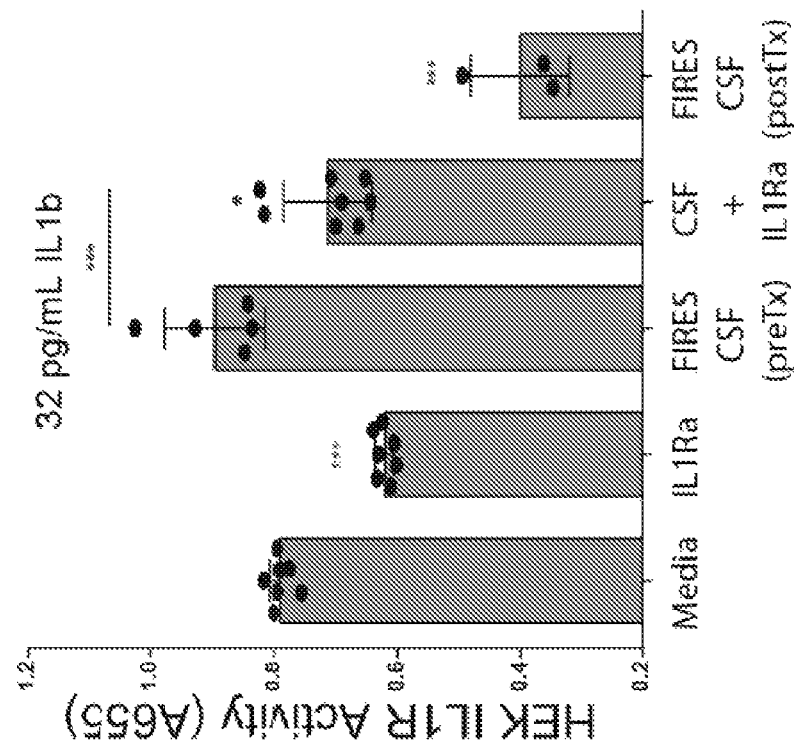

To investigate this possibility, the antagonistic activity of FIRES patient CSF-derived IL-1RA was assessed using an in vitro HEK-Blue IL1R cell-based assay. HEK-Blue IL1R cells cultured in media containing 50% control CSF or artificial CSF supplemented with recombinant IL-1RA did not show inhibition of IL-1R signaling, compared to HEK-Blue IL1R cells cultured in complete media (FIGS. 4A, 4B, and 4C). However, dialyzing CSF against DMEM/F12 using a 100 Dalton molecular weight cut off cellulose acetate membrane restored anakinra-mediated inhibition (FIG. 4D). Thus, HEK-Blue IL1R cells were treated with 32 pg/mL IL-1β in the presence of either 50% dialyzed FIRES patient CSF containing 65 pM patient IL-1RA or 50% dialyzed CSF derived from NPH patients that was supplemented with recombinant IL-1RA prior to dialysis to reach concentrations of IL-1RA equimolar to that seen in FIRES patient CSF. The percent inhibition of IL-1R-induced SEAP was then compared in cells treated with 50% CSF containing 65 pM FIRES patient IL-1RA vs. 50% CSF containing 65 pM anakinra. Surprisingly, FIRES patient CSF-derived IL-1RA was significantly less effective than recombinant IL-1RA (anakinra) at suppressing HEK IL-1R signaling (FIG. 5A). In contrast, treatment with NPH CSF supplemented with 65 pM anakinra showed significantly less IL-1R signaling in IL-1β treated HEK cells compared to unsupplemented NPH CSF (FIG. 5B). Importantly, FIRES patient CSF alone did not drive HEK IL-1R signaling (FIG. 5C), suggesting that the observed lack of IL-1R inhibition was not due to a concomitant increase in ligation of IL-1R by CSF derived agonists.

Example 6—Multiple Non-Coding Polymorphisms in FIRES Patient IL1RN Gene

Sanger sequencing was performed on overlapping 4000 bp amplicons spanning the IL1RN gene in FIRES patient DNA, but no variants were detected within the translated portion of the coding sequences. Several novel and known variants were detected within the intronic sequences and in the untranslated portion of exon 6. TABLE 1 lists each variant, along with its genomic location and associated risks for variants that were previously reported.

Figure 6B:
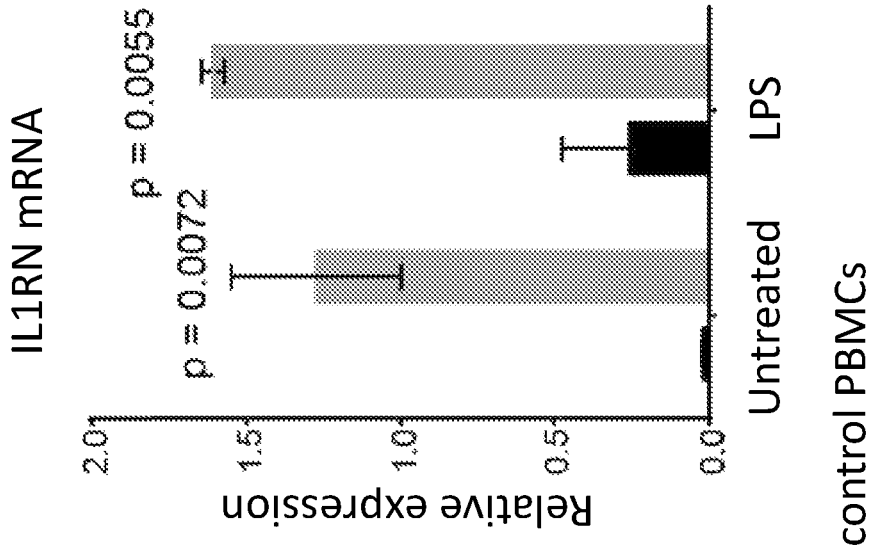
Figure 6C:
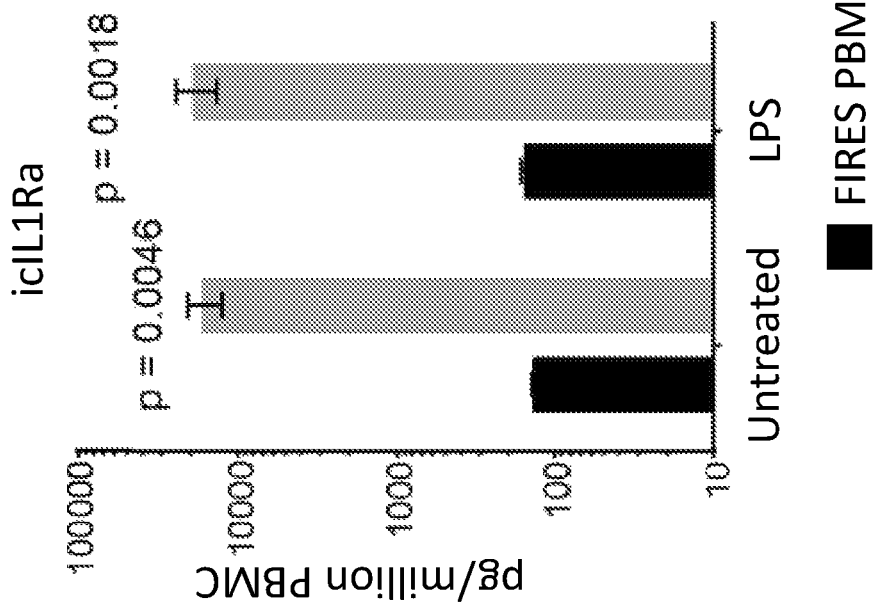
Figure 7C:
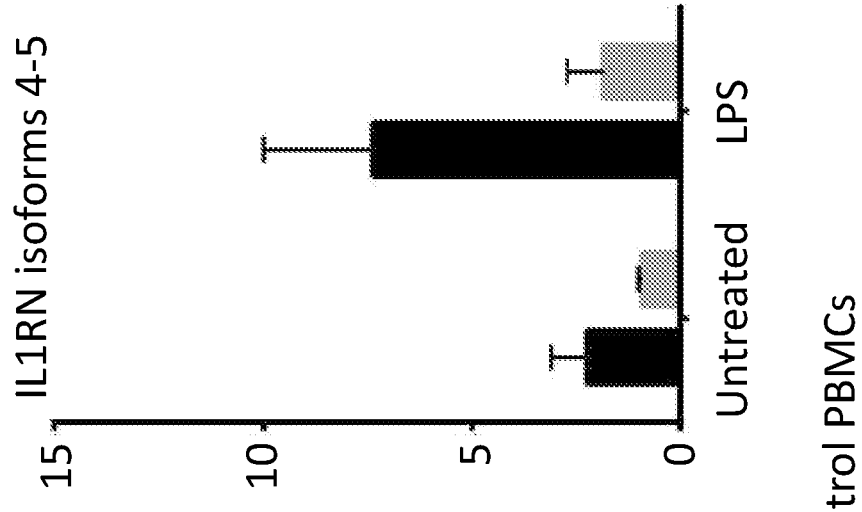
Figure 7D:
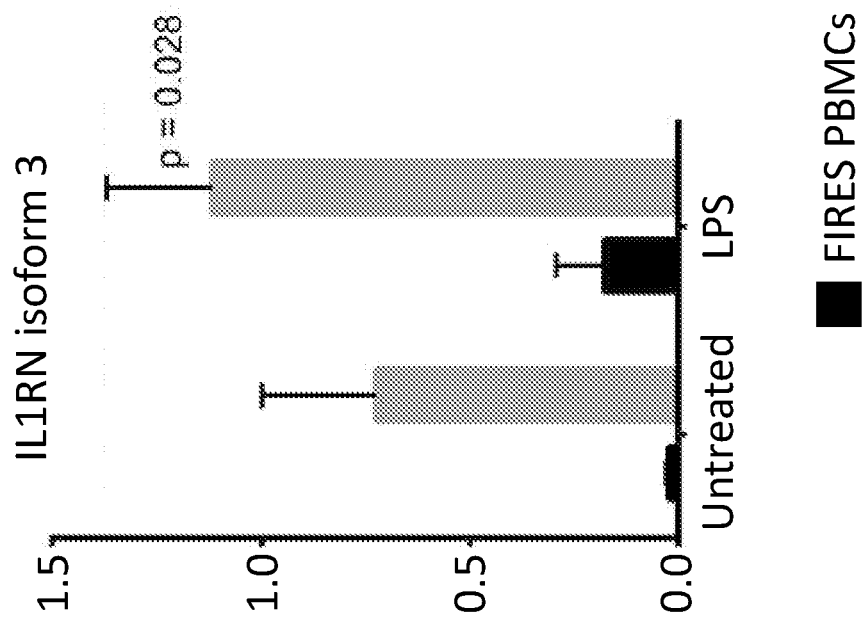
Figure 7E:
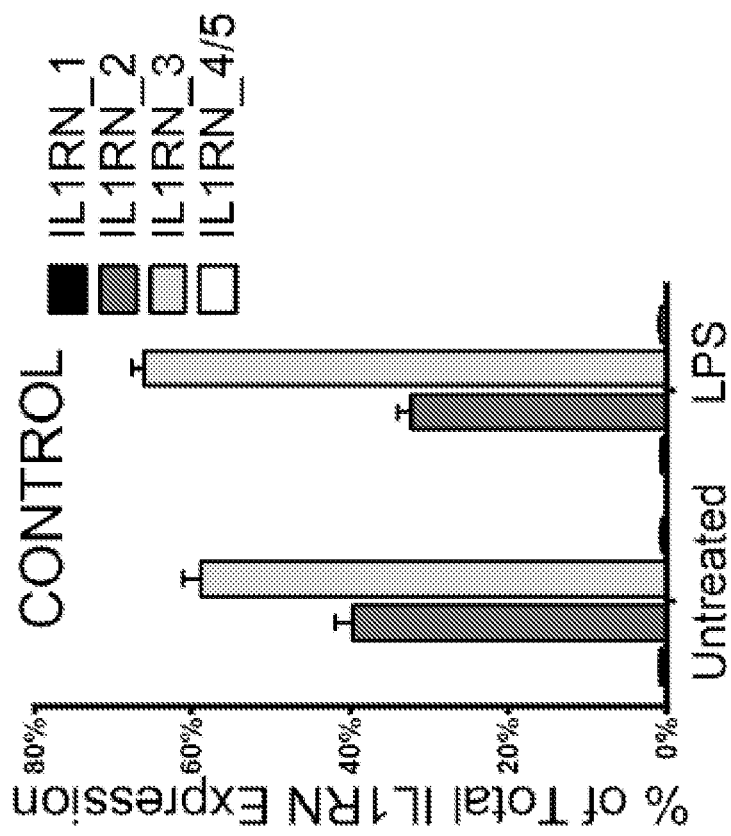
Figure 7F:
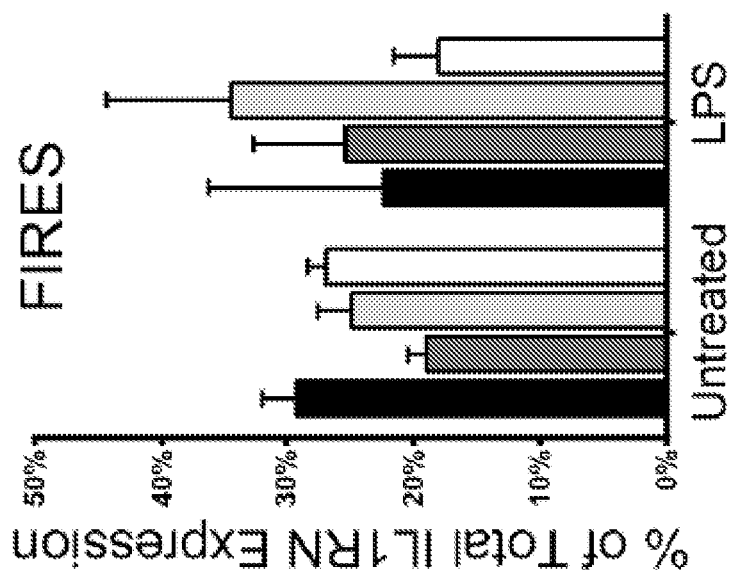

Example 7—Marked Reduction in Expression of Intracellular Isoforms of IL1RN in FIRES Patient PBMCs To determine whether there was aberrant expression of IL-1RA in FIRES, control and FIRES patient peripheral blood mononuclear cells (PBMCs) were isolated and treated with lipopolysaccharide (LPS) for 6 to 24 hours to ensure maximal IL-1RA production. In separate experiments, protein and RNA were isolated from cell lysates and collected supernatants. Secreted IL-1RA (isoforms 1 and 4/5) in cell supernatants and intracellular IL-1RA (isoforms 2 and 3) were measured by ELISA. Total IL1RN mRNA expression was determined by real time polymerase chain reaction (RTPCR). No differences were observed in the level of secreted IL-1RA between FIRES and control PBMCs (FIG. 6A), but the levels of intracellular IL-1RA were significantly reduced in FIRES PBMCs in both untreated and LPS-treated conditions (FIG. 6B). This corresponded with significantly reduced IL1RN mRNA levels in FIRES PBMCs relative to controls (FIG. 6C). IL-1RA is translated from five distinct isoforms that give rise to two secreted and two intracellular variants (the isoform 4 and 5 mRNA sequences only differ upstream of their translational start site). Importantly, the intracellular forms can be secreted in response to ATP and other triggers (see, Jeong et al., *Mediators Inflamm* 2016: 7984853; Wilson et al., *J Immunol* 173(2):1202-1208, 2004; and Evans et al., *Cytokine* 33(5):274-280, 2006). Thus, to determine whether the reduced intracellular levels of IL-1RA were due to aberrant expression of IL1RN isoforms in FIRES, expression of secreted (isoforms 1 and 4/5) and intracellular (isoforms 2 and 3) IL1RN gene products were analyzed by RTPCR. While IL1RN isoform 1 was somewhat increased following LPS stimulation in FIRES PBMCs relative to controls (FIG. 7A), this effect was small relative to the >10 fold reduced expression of isoform 2 (FIG. 7B) and isoform 3 (FIG. 7C) in FIRES PBMCs relative to control PBMCs. Differences between FIRES and control PBMCs in the total expression of isoforms 4 and 5 were not observed (FIG. 7D). The profound abrogation of expression of IL1RN isoforms 2 and 3 in FIRES patient PBMCS meant that these isoforms represented only 20% and 25%, respectively, of IL1RN expression in untreated conditions, jumping to a mere 25% and 35% of IL1RN expression after LPS treatment (FIG. 7E). In contrast, in control PBMCs these isoforms were the dominant IL1RN transcripts, together representing >95% of all expressed isoforms in both untreated and LPS treated conditions (FIG. 7F).

A representative amino acid sequence for isoform 1 of human IL-1RA is (SEQ ID NO: 42)
MEICRGLRSHLITLLLFLFHSETICRPSGRKSSKMQAFRIWDVNQKTFYL

RNNQLVAGYLQGPNVNLEEKIDVVPIEPHALFLGIHGGKMCLSCVKSGDE

TRLQLEAVNITDLSENRKQDKRFAFIRSDSGPTTSFESAACPGWFLCTAM

EADQPVSLTNMPDEGVMVTKFYFQEDE.

A representative amino acid sequence for isoform 1 of human IL-1RA is (SEQ ID NO: 43)
MALETICRPSGRKSSKMQAFRIWDVNQKTFYLRNNQLVAGYLQGPNVNLE

EKIDVVPIEPHALFLGIEGGKMCLSCVKSGDETRLQLEAVNITDLSENRK

QDKRFAFIRSDSGPTTSFESAACPGWFLCTAMEADQPVSLTNMPDEGVMV

TKFYFQEDE.

A representative amino acid sequence for isoform 3 of human IL-1RA is (SEQ ID NO: 44)
MALADLYEEGGGGGGEGEDNADSKETICRPSGRKSSKMQAFRIWDVNQKT

FYLRNNQLVAGYLQGPNVNLEEKIDVVPIEPHALFLGIHGGKMCLSCVKS

GDETRLQLEAVNITDLSENRKQDKRFAFIRSDSGPTTSFESAACPGWFLC

TAMEADQPVSLTNMPDEGVMVTKFYFQEDE.

A representative amino acid sequence for isoforms 4 and 5 of human IL-1RA is (SEQ ID NO: 45)
MQAFRIWDVNQKTFYLRNNQLVAGYLQGPNVNLEEKIDVVPIEPHALFLG

IHGGKMCLSCVKSGDETRLQLEAVNITDLSENRKQDKRFAFIRSDSGPTT

SFESAACPGWFLCTAMEADQPVSLTNMPDEGVMVTKFYFQEDE.

TABLE 1

IL1RN gene polymorphisms in FIRES patient

| Location (GRCh38.p7) | Location | Variation ID | Variant | Associated Risks/Notes |
|---|---|---|---|---|
| 113120414 | intron 2 | — | G > GT | |
| 113120473 | intron 2 | — | T > A | |
| 113121042 | intron 2 | — | dup TTC | |
| 113121075 | intron 2 | rs200489291 | del CTC | rs1553468945 = deletion at this site |
| 113121134 | intron 2 | — | C > A | |
| 113121077 | intron 2 | rs759842341 | del CTT | |
| 113121138 | intron 2 | rs377086 | A > G | |
| 113121321 | intron 2 | — | A > AT | |
| 113121720 | intron 2 | rs3213448 | G > A | increased IL1Ra levels |
| 113122472 | intron 2 | rs4251991 | T > G | |
| 113122715 | intron 2 | rs2853628 | C > G | |
| 113122916 | intron 2 | rs4251993 | G > A | |
| 113123788 | intron 2 | rs315935 | G > A | |

TABLE 1-continued

IL1RN gene polymorphisms in FIRES patient

| Location (GRCh38.p7) | Location | Variation ID | Variant | Associated Risks/Notes |
|---|---|---|---|---|
| 113124298 | intron 2 | — | T > TA | |
| 113126106 | intron 2 | rs4252001 | A > G | |
| 113126625 | intron 2 | rs3087262 | G > C | |
| 113126824 | intron 2 | rs439154 | A > G | childhood IgA nephropathy |
| 113128424 | intron 3 | — | ins T | |
| 113128430 | intron 3 | — | C > G | |
| 113128443 | intron 3 | — | T > G | |
| 113128472 | intron 3 | rs3181052 | G > A | increased risk of osteoarthritis progression |
| 113128773 | intron 3 | rs1794066 | A > G | increased risk of osteoarthritis progression |
| 113128807 | intron 3 | rs1794067 | A > G | increased risk of asthma |
| 113129906 | intron 4 | rs2071459 | C > T | increased risk of small bowel neuroendocrine tumor |
| 113130873 | intron 4 | — | T > A | rs910001631 = T > C at this site |
| 113130874 | intron 4 | — | ins CC | |
| 113130875 | intron 4 | — | G > T | |
| 113130888 | intron 4 | rs448341 | A > G | GVHD risk |
| 113130893 | intron 5 | rs434792 | C > T | |
| 113130905 | intron 4 | — | G > A | |
| 113130906 | intron 4 | rs020465621 | A > G | |
| 113130909 | intron 4 | — | del TG | |
| 113130910 | intron 4 | — | del TG | |
| 113131853 | intron 5 | rs315955 | G > C | cardiovascular disease |
| 113132211 | intron 5 | rs315954 | A > G | |
| 113132426 | intron 6 | rs315953 | C > T | |
| 113132727 | exon 6 | rs315952 | T > C | sterile multifocal osteomyelitis with periostitis and pustulosis, increased risk of acute coronary syndrome, systemic lupus erythematosus, and osteoarthritis severity |
| 113133009 | 3' UTR | rs315951 | C > G | sterile multifocal osteomyelitis with periostitis and pustulosis, increased risk of ulcerative colitis |
| 113133462 | | — | T > TG | |
| 113133680 | | — | G > GA | |

TABLE 2

IL1RN Primers

| IL1RN RTPCR primers | Direction | Sequence (SEQ ID NO: |
|---|---|---|
| IL1RN VNTR F | Forward | CTC AGC AAC ACT CCT AT (1) |
| IL1RN VNTR R | Reverse | TCC TGG TCT GCA GGT AA (2) |
| IL1RN_1F | Forward | AAC TCT GGG CCC GCA ATG (3) |
| IL1RN_2F | Forward | TGA CTC AAA GGA GAC GAT CTG (4) |
| IL1RN_3F | Forward | CAT GGC TTT AGA GAC GAT CTG C (5) |
| IL1RN_4-5F | Forward | TCA AAG CCA AGA AGG CAA GAG (6) |
| IL1RN_all isoforms FForward | | CAA GAT GCA AGC CTT CAG AAT C (7) |
| IL1RN_common R | Reverse | TCT GGT CTC ATC ACC AGA CT (8) |
| IL1RN PCR primers | Direction | Sequence |
| IL1RN FWD Set 1 | Forward | CAA ACC CTA ACT CAA TCC CAA AT (9) |
| IL1RN REV Set 1 | Reverse | AGG CAT TTT CAA GAT TTT ATT GTA AAA C (10) |
| IL1RN_1 FWD Set 1 | Forward | GGG CAG CTC CAC CCT GG (11) |
| IL1RN_1 REV Set 1 | Reverse | GTC CTG CCA AGT AGC CAA GTT AAT (12) |
| IL1RN FWD Set 9 | Forward | CAA GCT GGA TGC AAC CAT TTC (13) |
| IL1RN REV Set 9 | Reverse | GCC CTC AAA GGA AGA CAC TAT T (14) |
| IL1RN FWD Set 12 | Forward | TGC TAG CTG CCT TCT CTT TC (15) |

TABLE 2-continued

IL1RN Primers

| | | |
|---|---|---|
| IL1RN REV Set 12 | Reverse | GTG ACC AAG GGT CTG GAT TT (16) |
| IL1RN FWD Set 14 | Forward | CAT GGT GAA ACC CTG TCT CTA T (17) |
| IL1RN REV Set 14 | Reverse | GCC CAG CCC ATA ATC TAC TT (18) |
| IL1RN FWD Set 16 | Forward | CTG TGG GTG TAT GAG TGA CAA G (19) |
| IL1RN REV Set 16 | Reverse | GGA CTC TGG GAC CTA GGT TTA T (20) |
| IL1RN FWD Set 11 | Forward | AAC TCC AGC CAT CCT GAA TAA (21) |
| IL1RN REV Set 11 | Reverse | CCG TGT GAC CTT GAA CAA ATC (22) |
| IL1RN FWD Set 15 | Forward | CAT TCT CCT TTC TGG GTC TTA CT (23) |
| IL1RN REV Set 15 | Reverse | GAG TGC AGT GGA GCA ATC TA (24) |
| IL1RN FWD Set 5 | Forward | CGG GAT GGA CCC TGT TAT T (25) |
| IL1RN REV Set 5 | Reverse | GGT TCA GGC TAC TCT GTC TAT G (26) |

| IL1RN Sequencing | Direction | Sequence |
|---|---|---|
| IL1RN_14920F | Forward | ACC AAT ATG CCT GAC GAA GG (27) |
| IL1RN_15240F | Forward | TCT GCA TTC AGG ATC AAA CCC (28) |
| IL1RN_15787F | Forward | AGA AGT TTC TCA GCT CCC AAG G (29) |
| IL1RN_14578F | Forward | ATA AAC CTA GGT CCC AGA GTC C (30) |
| IL1RN_12921F | Forward | GAC ATC ACA TGG AAC ATC C (31) |
| IL1RN_9415F | Forward | CAG GAA CAG TAG GGA GTT TGG (32) |
| IL1RN_2043F | Forward | GGT GAG AAC AGA GGG TAA AGG (33) |
| IL1RN_66F | Forward | GCT CAG TTG AGT TAG AGT CTG G (34) |
| IL1RN_11430F | Forward | CTC AGA TGG GAA GCA AGT AAG G (35) |
| IL1RN_13355R | Reverse | GGA ACA GAA CTA CCC AGC TAA TC (36) |
| IL1RN_2965R | Reverse | CCC ACA CTA CAG TCC TAA A (37) |
| IL1RN_10549R | Reverse | TCG GCC CAG ACA AAC ATA AA (38) |
| IL1RN_513R | Reverse | GGC TCA GTG CCA CAT TCT ATT A (39) |
| IL1RN_15561R | Reverse | GAG TCC AGA TTA TGG AAG TG (40) |
| IL1RN_15484R | Reverse | ATC TCC AAA TGA AGG GCT CTC (41) |

Figure 8B:
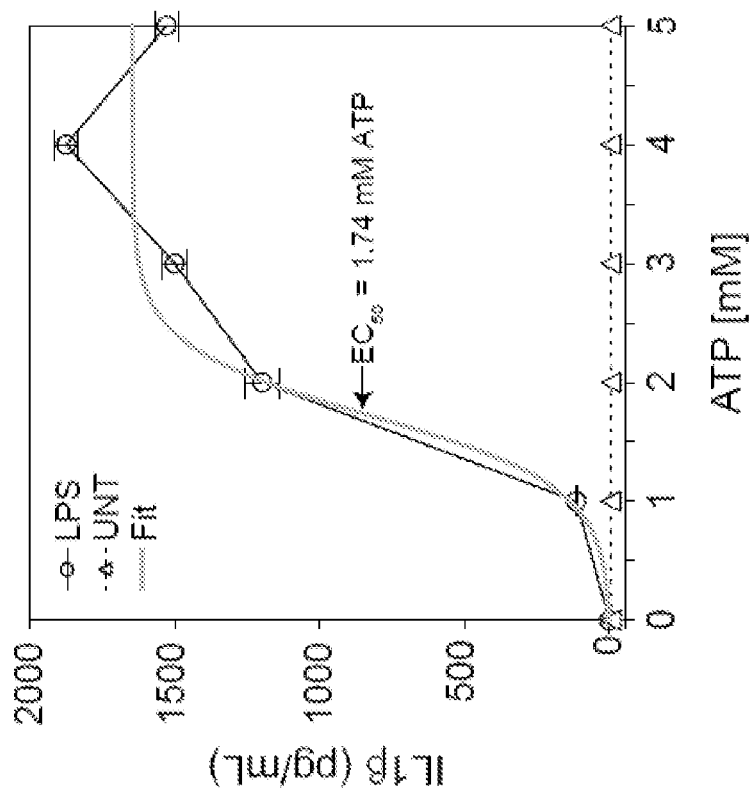
FIGS. 8A and 8B are graphs plotting cytokine production by neutrophils isolated from a 10 year old girl with periodic autoinflammatory disorder of unknown etiology. Neutrophils were primed with 100 ng/mL LPS for 90 minutes or left unprimed for the same amount of time. After priming, the cells were stimulated with 0-5 mM ATP for 45 minutes. After stimulation, cells were pelleted and supernatants were collected and clarified. Levels of tumor necrosis factor alpha (TNFα), IL-6, IL-1β, and IL-8 were measured and compared in supernatants from LPS-primed and unprimed neutrophils before (prestim) and after ATP stimulation.
Figure 8A:
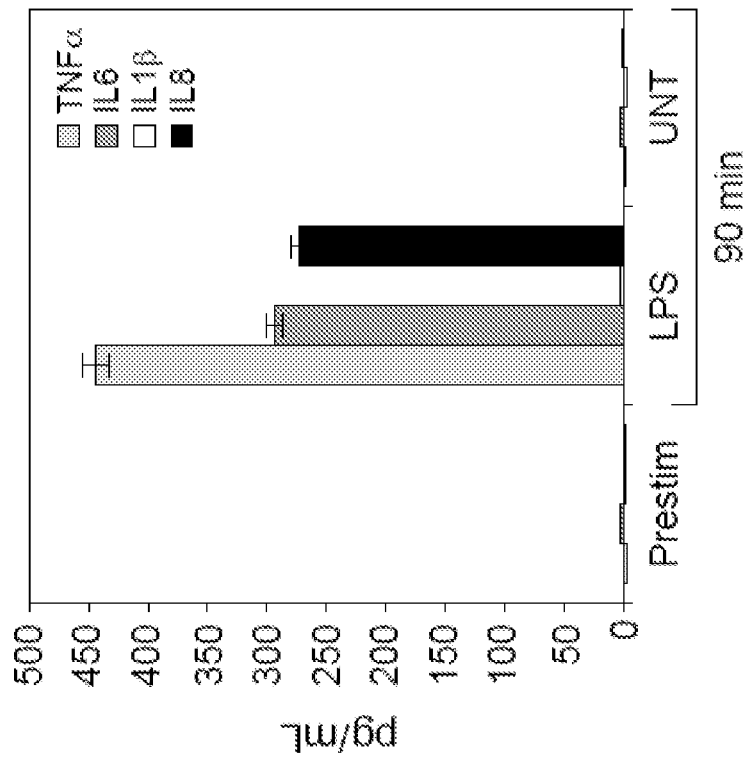

Example 8—Cytokine Production in Patient Neutrophils in Response to ATP Stimulation Blood was collected from a 10 year old girl with periodic autoinflammatory disorder of unknown etiology during disease remission. Neutrophils were enriched by density gradient centrifugation and then either primed with 100 ng/mL LPS for 90 minutes or left unprimed for the same amount of time. After priming, the cells were stimulated with a dose range of ATP (0-5 mM) for 45 minutes. At the end of stimulation, cells were pelleted and supernatants were collected and clarified. Cytokines (TNFα, IL-6, IL-1β, and IL-8) were measured using a multiplexed fluorescent bead array and quantified by comparison to standard curves. Levels of cytokines were compared in supernatants from LPS-primed and unprimed neutrophils before (prestim) and after ATP stimulation. Notably, LPS priming drove release of TNFα, IL-6, and IL-8, but did not directly induce IL-1β release (FIG. 8A). The response for these factors can serve as an addition marker of neutrophil responsivity. Supernatants from unprimed or primed neutrophils stimulated with different concentrations of ATP were then assessed for IL-1β release. While unprimed cells showed no response to ATP at any concentration (FIG. 8B), the primed cells exhibited robust IL-1β production and release at higher ATP concentrations. A 3-parameter sigmoidal curve was fit to the ATP response data, and the second differential of this curve was used to determine the $EC_{50}$ for ATP.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a subject having a seizure disorder, said method comprising determining that the subject has decreased IL-1RA function as compared to the level of IL-1RA function in corresponding normal subjects who do not have the seizure disorder, and administering to the subject a treatment that attenuates IL-1R inflammatory signaling, wherein said treatment comprises one or more of anakinra, EBI-005, and MEDI-8968.

2. The method of claim 1, wherein the treatment comprises anakinra.

3. The method of claim 1, wherein the seizure disorder is FIRES, PASS, DIRA, or MRE.

4. The method of claim 1, wherein the subject is a human child.

5. The method of claim 1, wherein the determining comprises measuring IL-1RA activity in a biological sample from the subject, wherein the biological sample comprises serum, serum microvesicles, or CSF, and determining that the IL-1RA activity in the biological sample is decreased relative to a corresponding control level of IL-1RA activity.

6. The method of claim 1, wherein the determining comprises measuring an inflammatory response in primed and stimulated neutrophils, monocytes, or PBMCs isolated from the subject, and determining that the measured inflammatory response is higher than an inflammatory response for control primed and stimulated neutrophils, monocytes, or PBMCs from subjects who do not have the seizure disorder.

7. The method of claim 6, comprising determining that the measured inflammatory response is at least two standard deviations higher than the inflammatory response for control primed and stimulated neutrophils, monocytes, or PBMCs from subjects who do not have the seizure disorder.

8. The method of claim 6, wherein the inflammatory response comprises secretion of IL-1β, IL-1RA, IL-18, IL-33, IL-36, IL-37, or IL-38 from the neutrophils, monocytes, or PBMCs after stimulation.

9. The method of claim 6, comprising priming the neutrophils, monocytes, or PBMCs with LPS.

10. The method of claim 6, comprising stimulating the neutrophils, monocytes, or PBMCs with ATP.

11. The method of claim 1, wherein the determining comprises measuring the relative amounts of IL-1RA (protein) or IL1RN (mRNA) isoforms in a biological sample from the subject, and determining that the subject has a ratio of soluble IL-1RA: intracellular IL-1RA that is increased relative to a control ratio of soluble IL-1RA: intracellular IL-1RA.

12. The method of claim 11, wherein the control ratio of soluble IL-1RA: intracellular IL-1RA is the ratio of soluble IL-1RA: intracellular IL-1RA in control subjects not having the seizure disorder.

13. A method for treating a subject having a seizure disorder, comprising identifying the subject as having a level of functional IL-1RA antagonism that is decreased below a predetermined threshold level of functional IL-1RA antagonism, and administering to the subject a treatment that attenuates IL-1R inflammatory signaling, wherein said treatment is selected from the group consisting of anakinra, EBI-005, and MEDI-8968.

14. The method of claim 13, wherein the treatment comprises anakinra.

15. The method of claim 13, wherein the seizure disorder is FIRES, PASS, DIRA, or MRE.

16. The method of claim 13, wherein the subject is a human child.

17. The method of claim 13, wherein the threshold level is 10% of the level of functional IL-1RA antagonism in corresponding control subjects who do not have the seizure disorder.

* * * * *

SEQUENCE LISTING

<160> NUMBER OF SEQ ID NOS: 45

<210> SEQ ID NO 1
<211> LENGTH: 17
<212> TYPE: DNA
<213> ORGANISM: Artificial Sequence
<220> FEATURE:
<223> OTHER INFORMATION: synthetic

<400> SEQUENCE: 1
ctcagcaaca ctcctat                                                 17

<210> SEQ ID NO 2
<211> LENGTH: 17
<212> TYPE: DNA
<213> ORGANISM: Artificial Sequence
<220> FEATURE:
<223> OTHER INFORMATION: synthetic

<400> SEQUENCE: 2
tcctggtctg caggtaa                                                 17

<210> SEQ ID NO 3
<211> LENGTH: 18
<212> TYPE: DNA
<213> ORGANISM: Artificial Sequence
<220> FEATURE:
<223> OTHER INFORMATION: synthetic

<400> SEQUENCE: 3
aactctgggc ccgcaatg                                                18

<210> SEQ ID NO 4
<211> LENGTH: 21
<212> TYPE: DNA
<213> ORGANISM: Artificial Sequence
<220> FEATURE:
<223> OTHER INFORMATION: synthetic

<400> SEQUENCE: 4
tgactcaaag gagacgatct g                                            21

<210> SEQ ID NO 5
<211> LENGTH: 22
<212> TYPE: DNA
<213> ORGANISM: Artificial Sequence
<220> FEATURE:
<223> OTHER INFORMATION: synthetic

<400> SEQUENCE: 5
catggcttta gagacgatct gc                                           22

<210> SEQ ID NO 6
<211> LENGTH: 21
<212> TYPE: DNA
<213> ORGANISM: Artificial Sequence
<220> FEATURE:
<223> OTHER INFORMATION: synthetic

<400> SEQUENCE: 6
tcaaagccaa gaaggcaaga g                                            21

<210> SEQ ID NO 7
<211> LENGTH: 22
<212> TYPE: DNA
<213> ORGANISM: Artificial Sequence

```
<220> FEATURE:
<223> OTHER INFORMATION: synthetic

<400> SEQUENCE: 7
caagatgcaa gccttcagaa tc                                              22

<210> SEQ ID NO 8
<211> LENGTH: 20
<212> TYPE: DNA
<213> ORGANISM: Artificial Sequence
<220> FEATURE:
<223> OTHER INFORMATION: synthetic

<400> SEQUENCE: 8
tctggtctca tcaccagact                                                 20

<210> SEQ ID NO 9
<211> LENGTH: 23
<212> TYPE: DNA
<213> ORGANISM: Artificial Sequence
<220> FEATURE:
<223> OTHER INFORMATION: synthetic

<400> SEQUENCE: 9
caaaccctaa ctcaatccca aat                                             23

<210> SEQ ID NO 10
<211> LENGTH: 28
<212> TYPE: DNA
<213> ORGANISM: Artificial Sequence
<220> FEATURE:
<223> OTHER INFORMATION: synthetic

<400> SEQUENCE: 10
aggcattttc aagattttat tgtaaaac                                        28

<210> SEQ ID NO 11
<211> LENGTH: 17
<212> TYPE: DNA
<213> ORGANISM: Artificial Sequence
<220> FEATURE:
<223> OTHER INFORMATION: synthetic

<400> SEQUENCE: 11
gggcagctcc accctgg                                                    17

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
gtcctgccaa gtagccaagt taat                                            24

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
caagctggat gccaacattt c                                               21
```

<210> SEQ ID NO 14
<211> LENGTH: 22
<212> TYPE: DNA
<213> ORGANISM: Artificial Sequence
<220> FEATURE:
<223> OTHER INFORMATION: synthetic

<400> SEQUENCE: 14
gccctcaaag gaagacacta tt     22

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
tgctagctgc cttctctttc     20

<210> SEQ ID NO 16
<211> LENGTH: 20
<212> TYPE: DNA
<213> ORGANISM: Artificial Sequence
<220> FEATURE:
<223> OTHER INFORMATION: synthetic

<400> SEQUENCE: 16
gtgaccaagg gtctggattt     20

<210> SEQ ID NO 17
<211> LENGTH: 22
<212> TYPE: DNA
<213> ORGANISM: Artificial Sequence
<220> FEATURE:
<223> OTHER INFORMATION: synthetic

<400> SEQUENCE: 17
catggtgaaa ccctgtctct at     22

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
gcccagccca taatctactt     20

<210> SEQ ID NO 19
<211> LENGTH: 22
<212> TYPE: DNA
<213> ORGANISM: Artificial Sequence
<220> FEATURE:
<223> OTHER INFORMATION: synthetic

<400> SEQUENCE: 19
ctgtgggtgt atgagtgaca ag     22

<210> SEQ ID NO 20
<211> LENGTH: 22
<212> TYPE: DNA
<213> ORGANISM: Artificial Sequence
<220> FEATURE:
<223> OTHER INFORMATION: synthetic

```
<400> SEQUENCE: 20
ggactctggg acctaggttt at                                              22

<210> SEQ ID NO 21
<211> LENGTH: 21
<212> TYPE: DNA
<213> ORGANISM: Artificial Sequence
<220> FEATURE:
<223> OTHER INFORMATION: synthetic

<400> SEQUENCE: 21
aactccagcc atcctgaata a                                               21

<210> SEQ ID NO 22
<211> LENGTH: 21
<212> TYPE: DNA
<213> ORGANISM: Artificial Sequence
<220> FEATURE:
<223> OTHER INFORMATION: synthetic

<400> SEQUENCE: 22
ccgtgtgacc ttgaacaaat c                                               21

<210> SEQ ID NO 23
<211> LENGTH: 23
<212> TYPE: DNA
<213> ORGANISM: Artificial Sequence
<220> FEATURE:
<223> OTHER INFORMATION: synthetic

<400> SEQUENCE: 23
cattctcctt tctgggtctt act                                             23

<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
gagtgcagtg gagcaatcta                                                 20

<210> SEQ ID NO 25
<211> LENGTH: 19
<212> TYPE: DNA
<213> ORGANISM: Artificial Sequence
<220> FEATURE:
<223> OTHER INFORMATION: synthetic

<400> SEQUENCE: 25
cgggatggac cctgttatt                                                  19

<210> SEQ ID NO 26
<211> LENGTH: 22
<212> TYPE: DNA
<213> ORGANISM: Artificial Sequence
<220> FEATURE:
<223> OTHER INFORMATION: synthetic

<400> SEQUENCE: 26
ggttcaggct actctgtcta tg                                              22

<210> SEQ ID NO 27
```

<211> LENGTH: 20
<212> TYPE: DNA
<213> ORGANISM: Artificial Sequence
<220> FEATURE:
<223> OTHER INFORMATION: synthetic

<400> SEQUENCE: 27
accaatatgc ctgacgaagg                                               20

<210> SEQ ID NO 28
<211> LENGTH: 21
<212> TYPE: DNA
<213> ORGANISM: Artificial Sequence
<220> FEATURE:
<223> OTHER INFORMATION: synthetic

<400> SEQUENCE: 28
tctgcattca ggatcaaacc c                                             21

<210> SEQ ID NO 29
<211> LENGTH: 22
<212> TYPE: DNA
<213> ORGANISM: Artificial Sequence
<220> FEATURE:
<223> OTHER INFORMATION: synthetic

<400> SEQUENCE: 29
agaagtttct cagctcccaa gg                                            22

<210> SEQ ID NO 30
<211> LENGTH: 22
<212> TYPE: DNA
<213> ORGANISM: Artificial Sequence
<220> FEATURE:
<223> OTHER INFORMATION: synthetic

<400> SEQUENCE: 30
ataaacctag gtcccagagt cc                                            22

<210> SEQ ID NO 31
<211> LENGTH: 19
<212> TYPE: DNA
<213> ORGANISM: Artificial Sequence
<220> FEATURE:
<223> OTHER INFORMATION: synthetic

<400> SEQUENCE: 31
gacatcacat ggaacatcc                                                19

<210> SEQ ID NO 32
<211> LENGTH: 21
<212> TYPE: DNA
<213> ORGANISM: Artificial Sequence
<220> FEATURE:
<223> OTHER INFORMATION: synthetic

<400> SEQUENCE: 32
caggaacagt agggagtttg g                                             21

<210> SEQ ID NO 33
<211> LENGTH: 21
<212> TYPE: DNA
<213> ORGANISM: Artificial Sequence
<220> FEATURE:
<223> OTHER INFORMATION: synthetic

<400> SEQUENCE: 33

```
ggtgagaaca gagggtaaag g                                         21

<210> SEQ ID NO 34
<211> LENGTH: 22
<212> TYPE: DNA
<213> ORGANISM: Artificial Sequence
<220> FEATURE:
<223> OTHER INFORMATION: synthetic

<400> SEQUENCE: 34
gctcagttga gttagagtct gg                                        22

<210> SEQ ID NO 35
<211> LENGTH: 22
<212> TYPE: DNA
<213> ORGANISM: Artificial Sequence
<220> FEATURE:
<223> OTHER INFORMATION: synthetic

<400> SEQUENCE: 35
ctcagatggg aagcaagtaa gg                                        22

<210> SEQ ID NO 36
<211> LENGTH: 23
<212> TYPE: DNA
<213> ORGANISM: Artificial Sequence
<220> FEATURE:
<223> OTHER INFORMATION: synthetic

<400> SEQUENCE: 36
ggaacagaac tacccagcta atc                                       23

<210> SEQ ID NO 37
<211> LENGTH: 19
<212> TYPE: DNA
<213> ORGANISM: Artificial Sequence
<220> FEATURE:
<223> OTHER INFORMATION: synthetic

<400> SEQUENCE: 37
cccacactac agtcctaaa                                            19

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
tcggcccaga caaacataaa                                           20

<210> SEQ ID NO 39
<211> LENGTH: 22
<212> TYPE: DNA
<213> ORGANISM: Artificial Sequence
<220> FEATURE:
<223> OTHER INFORMATION: synthetic

<400> SEQUENCE: 39
ggctcagtgc cacattctat ta                                        22

<210> SEQ ID NO 40
<211> LENGTH: 20
<212> TYPE: DNA
```

```
<213> ORGANISM: Artificial Sequence
<220> FEATURE:
<223> OTHER INFORMATION: synthetic

<400> SEQUENCE: 40
gagtccagat tatggaagtg                                                    20

<210> SEQ ID NO 41
<211> LENGTH: 21
<212> TYPE: DNA
<213> ORGANISM: Artificial Sequence
<220> FEATURE:
<223> OTHER INFORMATION: synthetic

<400> SEQUENCE: 41
atctccaaat gaagggctct c                                                  21

<210> SEQ ID NO 42
<211> LENGTH: 177
<212> TYPE: PRT
<213> ORGANISM: Homo sapiens

<400> SEQUENCE: 42

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 43
<211> LENGTH: 159
<212> TYPE: PRT
<213> ORGANISM: Homo sapiens

<400> SEQUENCE: 43

Met Ala Leu Glu Thr Ile Cys Arg Pro Ser Gly Arg Lys Ser Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45
```

```
Leu Glu Glu Lys Ile Asp Val Val Pro Ile Glu Pro His Ala Leu Phe
             50                  55                  60

Leu Gly Ile His Gly Gly Lys Met Cys Leu Ser Cys Val Lys Ser Gly
 65                  70                  75                  80

Asp Glu Thr Arg Leu Gln Leu Glu Ala Val Asn Ile Thr Asp Leu Ser
                 85                  90                  95

Glu Asn Arg Lys Gln Asp Lys Arg Phe Ala Phe Ile Arg Ser Asp Ser
                100                 105                 110

Gly Pro Thr Thr Ser Phe Glu Ser Ala Ala Cys Pro Gly Trp Phe Leu
            115                 120                 125

Cys Thr Ala Met Glu Ala Asp Gln Pro Val Ser Leu Thr Asn Met Pro
130                 135                 140

Asp Glu Gly Val Met Val Thr Lys Phe Tyr Phe Gln Glu Asp Glu
145                 150                 155

<210> SEQ ID NO 44
<211> LENGTH: 180
<212> TYPE: PRT
<213> ORGANISM: Homo sapiens

<400> SEQUENCE: 44

Met Ala Leu Ala Asp Leu Tyr Glu Glu Gly Gly Gly Gly Gly Gly Glu
 1               5                  10                  15

Gly Glu Asp Asn Ala Asp Ser Lys Glu Thr Ile Cys Arg Pro Ser Gly
                20                  25                  30

Arg Lys Ser Ser Lys Met Gln Ala Phe Arg Ile Trp Asp Val Asn Gln
             35                  40                  45

Lys Thr Phe Tyr Leu Arg Asn Asn Gln Leu Val Ala Gly Tyr Leu Gln
 50                  55                  60

Gly Pro Asn Val Asn Leu Glu Glu Lys Ile Asp Val Val Pro Ile Glu
 65                  70                  75                  80

Pro His Ala Leu Phe Leu Gly Ile His Gly Gly Lys Met Cys Leu Ser
                 85                  90                  95

Cys Val Lys Ser Gly Asp Glu Thr Arg Leu Gln Leu Glu Ala Val Asn
                100                 105                 110

Ile Thr Asp Leu Ser Glu Asn Arg Lys Gln Asp Lys Arg Phe Ala Phe
            115                 120                 125

Ile Arg Ser Asp Ser Gly Pro Thr Thr Ser Phe Glu Ser Ala Ala Cys
130                 135                 140

Pro Gly Trp Phe Leu Cys Thr Ala Met Glu Ala Asp Gln Pro Val Ser
145                 150                 155                 160

Leu Thr Asn Met Pro Asp Glu Gly Val Met Val Thr Lys Phe Tyr Phe
                165                 170                 175

Gln Glu Asp Glu
            180

<210> SEQ ID NO 45
<211> LENGTH: 143
<212> TYPE: PRT
<213> ORGANISM: Homo sapiens

<400> SEQUENCE: 45

Met Gln Ala Phe Arg Ile Trp Asp Val Asn Gln Lys Thr Phe Tyr Leu
 1               5                  10                  15

Arg Asn Asn Gln Leu Val Ala Gly Tyr Leu Gln Gly Pro Asn Val Asn
                20                  25                  30
```

```
Leu Glu Glu Lys Ile Asp Val Val Pro Ile Glu Pro His Ala Leu Phe
        35              40              45

Leu Gly Ile His Gly Gly Lys Met Cys Leu Ser Cys Val Lys Ser Gly
    50              55              60

Asp Glu Thr Arg Leu Gln Leu Glu Ala Val Asn Ile Thr Asp Leu Ser
65              70              75              80

Glu Asn Arg Lys Gln Asp Lys Arg Phe Ala Phe Ile Arg Ser Asp Ser
            85              90              95

Gly Pro Thr Thr Ser Phe Glu Ser Ala Ala Cys Pro Gly Trp Phe Leu
            100             105             110

Cys Thr Ala Met Glu Ala Asp Gln Pro Val Ser Leu Thr Asn Met Pro
        115             120             125

Asp Glu Gly Val Met Val Thr Lys Phe Tyr Phe Gln Glu Asp Glu
    130             135             140
```